United States Patent
Hanagata et al.

(10) Patent No.: US 10,449,212 B2
(45) Date of Patent: Oct. 22, 2019

(54) IMMUNOSTIMULATING OLIGONUCLEOTIDE COMPLEX

(71) Applicants: NATIONAL INSTITUTE FOR MATERIALS SCIENCE, Tsukuba-shi, Ibaraki (JP); Denka Company Limited, Tokyo (JP)

(72) Inventors: Nobutaka Hanagata, Tsukuba (JP); Hiroshi Otsuka, Tokyo (JP); Takafumi Harada, Tokyo (JP)

(73) Assignees: NATIONAL INSTITUTE FOR MATERIALS SCIENCE, Tsukuba-Shi, Ibaraki (JP); DENKA COMPANY LIMITED, Chuo-Ku, Tokyo (JP)

( * ) Notice: Subject to any disclaimer, the term of this patent is extended or adjusted under 35 U.S.C. 154(b) by 0 days.

(21) Appl. No.: 15/740,667

(22) PCT Filed: Jul. 8, 2016

(86) PCT No.: PCT/JP2016/070293
§ 371 (c)(1),
(2) Date: Dec. 28, 2017

(87) PCT Pub. No.: WO2017/007027
PCT Pub. Date: Jan. 12, 2017

(65) Prior Publication Data
US 2018/0193371 A1 Jul. 12, 2018

(30) Foreign Application Priority Data
Jul. 9, 2015 (JP) .................. 2015-138004

(51) Int. Cl.
| | |
|---|---|
| C07H 21/04 | (2006.01) |
| A61K 31/713 | (2006.01) |
| A61K 39/39 | (2006.01) |
| C12N 15/09 | (2006.01) |
| C12N 15/117 | (2010.01) |
| A61K 47/68 | (2017.01) |
| A61P 37/08 | (2006.01) |
| A61P 35/00 | (2006.01) |

(52) U.S. Cl.
CPC ........... *A61K 31/713* (2013.01); *A61K 39/39* (2013.01); *A61K 47/6807* (2017.08); *A61P 35/00* (2018.01); *A61P 37/08* (2018.01); *C12N 15/09* (2013.01); *C12N 15/117* (2013.01)

(58) Field of Classification Search
None
See application file for complete search history.

(56) References Cited

U.S. PATENT DOCUMENTS

| | | | | |
|---|---|---|---|---|
| 7,585,847 B2 * | 9/2009 | Bratzler | ............... | A61K 31/138 424/130.1 |
| 8,304,396 B2 | 11/2012 | Krieg et al. | | |
| 2004/0014956 A1 * | 1/2004 | Woolf | ............... | A61K 31/713 536/23.1 |
| 2004/0198688 A1 | 10/2004 | Krieg et al. | | |
| 2005/0001055 A1 | 1/2005 | Gebhardt | | |
| 2005/0130911 A1 | 6/2005 | Uhlmann et al. | | |
| 2006/0140875 A1 | 6/2006 | Krieg et al. | | |
| 2006/0182793 A1 * | 8/2006 | Bachmann | ............. | A61K 9/127 424/450 |
| 2008/0045473 A1 | 2/2008 | Uhlmann et al. | | |

FOREIGN PATENT DOCUMENTS

| | | |
|---|---|---|
| JP | 2007-500018 A | 1/2007 |
| JP | 2007-506790 A | 3/2007 |
| JP | 2008-516634 A | 5/2008 |
| JP | 2009-528027 A | 8/2009 |
| JP | 2012200233 | 10/2012 |

OTHER PUBLICATIONS

Gungor, Bilgi et al., "CpG ODN Nanorings Induce IFNα from Plasmacytoid Dendritic Cells and Demonstrate Potent Vaccine Adjuvant Activity," Science Translational Medicine, vol. 6, No. 235, 2014, 11 pages.
Hartmann, Gunther et al., "Delineation of CpG Phosphorothioate Oligodeoxynucleotide for Activating Primate Immune Responses In Vitro and In Vivo," J. Immunol., vol. 164, 2000, pp. 1617-1624.
International Search Report dated Oct. 11, 2016 for International Application No. PCT/JP2016/070293, 13 pages.
Klein, Dionne C.G. et al., "Higher Order Structure of Short Immunostimulatory Oligonucleotides Studied by Atomic Force Microscopy," Ultramicroscopy, vol. 110, 2010, pp. 689-693.
Krug, Anne et al., "Identification of CpG Oligonucleotide Sequences with High Induction of IFN-α/β in Plasmacytoid Dendritic Cells," Eur. J. Immunol., vol. 31, pp. 2154-2163.
Meng, Wenjun et al., "Nuclease-Resistant Immunostimulatory Phosphodiester CpG Oligodeoxynucleotides as Human Toll-like Receptor 9 Agonists," BMC Biotechnology, vol. 11, No. 88, 2011, 9 pages.
Poeck, Hendrik et al., "Plasmacytoid Dendritic Cells, Antigen, and CpG-C License Human B Cells for Plasma Cell Differentiation and Immunoglobulin Production in the Absence of T-cell Help," Blood Journal, vol. 103, No. 8, 2004, pp. 3058-3064.
Hanagata, Nobutaka, "Recognition of Oligodeoxynucleotides by Toll-like Receptor 9: Phosphodiester Backbone vs. Phosphorothioate Backbone and Monomer vs. Multimer," Nano Biomedics, vol. 5, No. 2, 2013, pp. 55-63.

(Continued)

*Primary Examiner* — Kimberly Chong
(74) *Attorney, Agent, or Firm* — Brinks Gilson & Lione

(57) ABSTRACT

Provided is an immunostimulating oligonucleotide that is suitable for industrial production and has an excellent type-I IFN inducing activity even when not modified to become a phosphorothioate. This linear double-stranded oligonucleotide contains 10-100 base pairs, wherein the single-stranded oligonucleotides constituting the double-stranded oligonucleotide each contain 2-20 phosphodiester-mediated cytosine-guanine (CpG) sequences, and at least 90% of the internucleotide bonds in each single-stranded oligonucleotide are phosphodiester bonds.

15 Claims, 12 Drawing Sheets

Specification includes a Sequence Listing.

(56) References Cited

OTHER PUBLICATIONS

Domeika et al., "Characteristics of oligodeoxyribonucleotides that induce interferon (IFN)-alpha in the pig and the phenotype of the IFN-alpha producing cells" Veterinary Immunology and Immunopathology, vol. 1, No. 1-2, Sep. 2004, pp. 87-102.

Roberts, et al., "Differences in macrophage activation by bacterial DNA and CpG-containing oligonucleotides" Journal of Immunology, Vo. 175, No. 6, Sep. 2005, pp. 3569-3576.

Magnusson et al., "Importance of CpG dinucleotides in activation of natural IFN-alpha-producing cells by a lupus-related oligodeoxynucleotide" Scandinavian Journal of Immunology, vol. 54, No. 6, Dec. 2001, pp. 543-550.

European Patent Office, Extended European Search Report for European Application No. 16821495.5 dated Mar. 2, 2018 pp. 1-9.

* cited by examiner

```
                        SEQUENCE LISTING

<160> NUMBER OF SEQ ID NOS: 28

<210> SEQ ID NO 1
<211> LENGTH: 24
<212> TYPE: DNA
<213> ORGANISM: Artificial Sequence
<220> FEATURE:
<223> OTHER INFORMATION: all PD 24-base single strand CpG ODN

<400> SEQUENCE: 1
tcgtcgtttt gtcgttttgt cgtt                                          24

<210> SEQ ID NO 2
<211> LENGTH: 48
<212> TYPE: DNA
<213> ORGANISM: Artificial Sequence
<220> FEATURE:
<223> OTHER INFORMATION: all PD 48-base single strand ODN

<400> SEQUENCE: 2
tcgtcgtttt gtcgttttgt cgtttcgtcg ttttgtcgtt ttgtcgtt               48

<210> SEQ ID NO 3
<211> LENGTH: 72
<212> TYPE: DNA
<213> ORGANISM: Artificial Sequence
<220> FEATURE:
<223> OTHER INFORMATION: all PD 72-base single strand ODN

<400> SEQUENCE: 3
tcgtcgtttt gtcgttttgt cgtttcgtcg ttttgtcgtt ttgtcgtttc gtcgttttgt   60
cgttttgtcg tt                                                       72

<210> SEQ ID NO 4
<211> LENGTH: 20
<212> TYPE: DNA
<213> ORGANISM: Artificial Sequence
<220> FEATURE:
<223> OTHER INFORMATION: all PD 20-base single strand CpG ODN

<400> SEQUENCE: 4
atcgactctc gagcgttctc                                               20

<210> SEQ ID NO 5
<211> LENGTH: 24
<212> TYPE: DNA
<213> ORGANISM: Artificial Sequence
<220> FEATURE:
<223> OTHER INFORMATION: all PT 24-base single strand CpG ODN

<400> SEQUENCE: 5
tcgtcgtttt gtcgttttgt cgtt                                          24

<210> SEQ ID NO 6
<211> LENGTH: 48
<212> TYPE: DNA
<213> ORGANISM: Artificial Sequence
<220> FEATURE:
<223> OTHER INFORMATION: all PT 48-base single strand CpG ODN

<400> SEQUENCE: 6
tcgtcgtttt gtcgttttgt cgtttcgtcg ttttgtcgtt ttgtcgtt               48
```

<210> SEQ ID NO 7
<211> LENGTH: 72
<212> TYPE: DNA
<213> ORGANISM: Artificial Sequence
<220> FEATURE:
<223> OTHER INFORMATION: all PT 72-base single strand CpG ODN

<400> SEQUENCE: 7
tcgtcgtttt gtcgttttgt cgtttcgtcg ttttgtcgtt ttgtcgtttc gtcgttttgt        60
cgttttgtcg tt                                                            72

<210> SEQ ID NO 8
<211> LENGTH: 20
<212> TYPE: DNA
<213> ORGANISM: Artificial Sequence
<220> FEATURE:
<223> OTHER INFORMATION: all PT 20-base single strand CpG ODN

<400> SEQUENCE: 8
atcgactctc gagcgttctc                                                    20

<210> SEQ ID NO 9
<211> LENGTH: 24
<212> TYPE: DNA
<213> ORGANISM: Artificial Sequence
<220> FEATURE:
<223> OTHER INFORMATION: all PD CpG-free single strand ODN

<400> SEQUENCE: 9
tcagagagtt agagagttag agag                                               24

<210> SEQ ID NO 10
<211> LENGTH: 48
<212> TYPE: DNA
<213> ORGANISM: Artificial Sequence
<220> FEATURE:
<223> OTHER INFORMATION: all PD 48-base CpG-free single strand ODN

<400> SEQUENCE: 10
tcagagagtt agagagttag agagtcagag agttagagag ttagagag                     48

<210> SEQ ID NO 11
<211> LENGTH: 72
<212> TYPE: DNA
<213> ORGANISM: Artificial Sequence
<220> FEATURE:
<223> OTHER INFORMATION: all PD 72-base CpG-free single strand ODN

<400> SEQUENCE: 11
tcagagagtt agagagttag agagtcagag agttagagag ttagagagtc agagagttag        60
agagttagag ag                                                            72

<210> SEQ ID NO 12
<211> LENGTH: 20
<212> TYPE: DNA
<213> ORGANISM: Artificial Sequence
<220> FEATURE:
<223> OTHER INFORMATION: CpG-A having palindrome sequence with each
      terminal PT connected poly-g

<400> SEQUENCE: 12
gggggacgat cgtcggggggg                                                   20

<210> SEQ ID NO 13

```
<211> LENGTH: 20
<212> TYPE: DNA
<213> ORGANISM: Artificial Sequence
<220> FEATURE:
<223> OTHER INFORMATION: CpG-A having palindrome sequence with each
      terminal PT connected poly-g

<400> SEQUENCE: 13 gggggtcaacg ttgagggggg                                              20

<210> SEQ ID NO 14
<211> LENGTH: 20
<212> TYPE: DNA
<213> ORGANISM: Artificial Sequence
<220> FEATURE:
<223> OTHER INFORMATION: CpG-A having palindrome sequence with each
      terminal PT connected poly-g

<400> SEQUENCE: 14
ggtgcatcga tgcaggggg                                                20

<210> SEQ ID NO 15
<211> LENGTH: 20
<212> TYPE: DNA
<213> ORGANISM: Artificial Sequence
<220> FEATURE:
<223> OTHER INFORMATION: CpG-B all PT

<400> SEQUENCE: 15
tccatgacgt tcctgacgtt                                               20

<210> SEQ ID NO 16
<211> LENGTH: 20
<212> TYPE: DNA
<213> ORGANISM: Artificial Sequence
<220> FEATURE:
<223> OTHER INFORMATION: CpG-B all PT

<400> SEQUENCE: 16
atcgactctc gagcgttctc                                               20

<210> SEQ ID NO 17
<211> LENGTH: 22
<212> TYPE: DNA
<213> ORGANISM: Artificial Sequence
<220> FEATURE:
<223> OTHER INFORMATION: CpG-C having all PT connected palindrome
      sequence

<400> SEQUENCE: 17
tcgtcgtttt cggcgcgcgc cg                                            22

<210> SEQ ID NO 18
<211> LENGTH: 72
<212> TYPE: DNA
<213> ORGANISM: Artificial Sequence
<220> FEATURE:
<223> OTHER INFORMATION: B72M1-PD

<400> SEQUENCE: 18
tcgtcgtttt gtcgttttgt cgtttcgtcg ttttgtcgtt ttgtcgtttc gtcgttttgt   60
cgttctgttc ac                                                       72

<210> SEQ ID NO 19
<211> LENGTH: 72
<212> TYPE: DNA
```

```
<213> ORGANISM: Artificial Sequence
<220> FEATURE:
<223> OTHER INFORMATION: B72M2-PD

<400> SEQUENCE: 19
tcgtcgtttt gtcgttttgt cgtttcgtcg ttttgtcgtt ttgtcgtttc gtcgttttgt       60
cgttctcgtc ac                                                          72

<210> SEQ ID NO 20
<211> LENGTH: 72
<212> TYPE: DNA
<213> ORGANISM: Artificial Sequence
<220> FEATURE:
<223> OTHER INFORMATION: B72M3-PD

<400> SEQUENCE: 20
tcgtcgtttt gtcgttttgt cgtttcgtcg ttctcgtcac ttgtcgtttc gtcgttttgt       60
cgttctgttc ac                                                          72

<210> SEQ ID NO 21
<211> LENGTH: 72
<212> TYPE: DNA
<213> ORGANISM: Artificial Sequence
<220> FEATURE:
<223> OTHER INFORMATION: B72M4-PD

<400> SEQUENCE: 21
tcgtcgtttt gtcgttttgt cgtttcgtcg tttctgttca ctgtcgtttc gtcgttttgt       60
cgttctcgtc ac                                                          72

<210> SEQ ID NO 22
<211> LENGTH: 72
<212> TYPE: DNA
<213> ORGANISM: Artificial Sequence
<220> FEATURE:
<223> OTHER INFORMATION: B72M5-PD

<400> SEQUENCE: 22
tcgtcgtttt gtcgttttgt cgtttcgtcg tttctcgtca ctgtcgtttc gtcgttttgt       60
cgttctcgtc ac                                                          72

<210> SEQ ID NO 23
<211> LENGTH: 48
<212> TYPE: DNA
<213> ORGANISM: Artificial Sequence
<220> FEATURE:
<223> OTHER INFORMATION: B48M1-PD

<400> SEQUENCE: 23
tcgtcgtttt gtcgttttgt cgtttcgtcg ttttgtcgtt ctgttcac                    48

<210> SEQ ID NO 24
<211> LENGTH: 48
<212> TYPE: DNA
<213> ORGANISM: Artificial Sequence
<220> FEATURE:
<223> OTHER INFORMATION: B48M2-PD

<400> SEQUENCE: 24
tcgtcgtttt gtcgttttgt cgtttcgtcg ttttgtcgtt ctcgtcac                    48

<210> SEQ ID NO 25
<211> LENGTH: 48
```

```
<212> TYPE: DNA
<213> ORGANISM: Artificial Sequence
<220> FEATURE:
<223> OTHER INFORMATION: B48M3-PD

<400> SEQUENCE: 25
tcgtcgttct cgtcacttgt cgtttcgtcg ttttgtcgtt ctgttcac                48

<210> SEQ ID NO 26
<211> LENGTH: 48
<212> TYPE: DNA
<213> ORGANISM: Artificial Sequence
<220> FEATURE:
<223> OTHER INFORMATION: B48M4-PD

<400> SEQUENCE: 26
tcgtcgtttc tgttcactgt cgtttcgtcg ttttgtcgtt ctcgtcac                48

<210> SEQ ID NO 27
<211> LENGTH: 48
<212> TYPE: DNA
<213> ORGANISM: Artificial Sequence
<220> FEATURE:
<223> OTHER INFORMATION: B48M5-PD

<400> SEQUENCE: 27
tcgtcgtttc tcgtcactgt cgtttcgtcg ttttgtcgtt ctcgtcac                48

<210> SEQ ID NO 28
<211> LENGTH: 48
<212> TYPE: DNA
<213> ORGANISM: Artificial Sequence
<220> FEATURE:
<223> OTHER INFORMATION: CpG48-PD

<400> SEQUENCE: 28
tcaacgtcta cgagacgacg tacgttcgaa cgtccacgta tcgtacgt                48
```

IMMUNOSTIMULATING OLIGONUCLEOTIDE COMPLEX

This application is a 371 application of PCT/JP2016/070293 having an international filing date of Jul. 8, 2016, which claims priority to JP2015-138004 filed Jul. 9, 2015, the entire content of each of which is incorporated herein by reference.

TECHNICAL FIELD

The present invention relates to an immunostimulating oligonucleotide complex, and specifically to a complex which is formed by combining a double-stranded oligonucleotide and a carrier, has excellent inducing activity for type-I interferons including interferon-α (IFN-α) and interferon-β (IFN-β), and interleukin-12 (IL-12), and works as an adjuvant.

BACKGROUND ART

Innate immunity is biogenic initial defense reaction against microbial infection. Microbial components cause various immune responses through recognition by receptors such as Toll-like receptors (TLRs), NOD-like receptors (NLRs), RIG-I-like receptors (RLRs), DNA-dependent activator of IFN-regulatory factors (DAI), IFN-γ-inducible protein 16 (IFI16), DDX41, and cyclic GMP-AMP synthase (cGAS).

Toll-like receptors (TLRs) are one-pass transmembrane receptors which form homo dimers or hetero dimers through bonding with ligands, and transmit signals. Human has 10 types of TLRs, and those of which that recognize nucleic acid are TLR3 (recognizes double helical RNA), TLR7 and TLR8 (recognize single-strand RNA), and TLR9 (recognizes unmethylated CpG DNA). TLR3, TLR7, TLR8, and TLR9 are mainly localized in intracellular organelle membranes of ERs and endosomes, and recognize ligands in endosomes, and transmit signals. On the other hand, TLR1 (recognizes triacyl lipoprotein and others), TLR2 (recognizes peptidoglycan and others), TLR4 (recognizes lipopolysaccharide and others), TLR5 (recognizes flagellin and others), and TLR6 (recognizes diacyl lipoprotein and others) which recognize sugars, lipids, and proteins derived from bacteria and viruses are localized on cell surfaces, recognize the microbial surface components and transmit signals on the cell surfaces.

NOD-like receptors (NLRB) are intracellular receptors composing 30 or more large families. They mainly recognize specifically peptidoglycan derived from microorganisms.

RIG-I-like receptors (RLRs) belong to an intracytoplasmic RNA helicase family, and recognize RNAs found in cytoplasm.

DNA-dependent activator of IFN-regulatory factors (DAI), IFN-γ-inducible protein 16 (IFI16), DDX41, cyclic GMP-AMP synthase (cGAS) are identified as cytosolic DNA receptors, but the presence of other cytosolic DNA receptors is suggested.

As described above, various receptors are involved in immunoactivity individually or in collaboration, but the full facts have not been clarified.

Infection, cancer, and allergy are improved by enhancing immunoactivity. For these diseases, research and development for using synthetic oligodeoxynucleotides (hereinafter may be referred to as "ODNs") containing an unmethylated cytosine-guanine sequence (CpG) as immune-activating medicines have been actively carried out since 2000. The CpG ODNs developed heretofore are largely classified into three classes (class A, class B, and class C).

The CpG-A ODN of class A (also referred to as D type) is a single-stranded ODN which contains CpG in the palindrome sequence with the phosphodiester sugar backbone, and the polyguanine sequence with the phosphorothioated sugar backbone is added to both terminals of the CpG-A ODN (3' and 5' terminals) (for example, ODN2216, ODN1585, and D35 shown in Table 1). Two molecules of CpG-A ODN complementarily form a double strand by the palindrome sequence of its phosphodiester sugar backbone, and the polyguanine sequences at both ends form guanine tetramers, so that the two double-stranded CpG-A ODNs are self-assembled to form a tetramer. These tetramers are further self-assembled to double-stranded CpG-A ODN and single-stranded CpG-A ODN molecules, thus forming a higher-order structure (Non-Patent Literature 1). The CpG-A ODN is recognized mainly by TLR9, which are dendritic cells, and induces type-I interferons (IFNs) such as interferon-α (IFN-α) and interferon-β (IFN-β) (Patent Literature 1, and Non-Patent Literature 2).

The CpG-B ODN of class B (also referred to K type) is a single-stranded ODN composed entirely of a phosphorothioated sugar backbone containing CpG (for example, see ODN1826, ODN2006, and K3 shown in Table 1). The CpG-B ODN is mainly recognized by TLR9 of B cells, and induces inflammatory cytokines such as interleukin-6 (IL-6) or IL-12, or tumor necrosis factors (TNFs) (Non-Patent Literature 3). It is known that a complex formed by electrostatically bonding CpG-B ODN with a cationic peptide or cationic liposome induces type-I IFN in the same manner as CpG-A (Non-Patent Literature 4).

The CpG-C ODN of class C is a single-stranded ODN composed entirely of a phosphorothioated sugar backbone containing a palindrome sequence at the 3' terminal side, and contains CpG at both of the 5' terminal and 3' terminal (for example, ODN2395 shown in Table 1). The CpG-C ODN forms a partially double strand from two molecules by its palindrome sequence. The CpG-C ODN exhibits an intermediate nature between CpG-A and CpG-B, and induces both of inflammatory cytokine and type-I IFN (Non-Patent Literature 5).

TABLE 1

Table 1. Major CpG DNAs ever developed

| Class | Name (sequence No) | Sequence *) | Subject |
|---|---|---|---|
| A | ODN2216 (12) | 5'-ggGGGACGATCGTCgggggg-3' | Human |
| A | ODN1585 (13) | 5'-ggGGTCAACGTTGAgggggg-3' | Mouse |
| A | D35 (14) | 5'-ggTGCATCGATGCAGGGGgg-3' | Human, mouse |
| B | ODN1826 (15) | 5'-tccatgacgttcctgacgtt-3' | Mouse |
| B | ODN2006 (5) | 5'-tcgtcgttttgtcgttttgtcgtt-3' | Human |
| B | K3 (16) | 5'-atcgactctcgagcgttctc-3' | Human, mouse |

TABLE 1-continued

Table 1. Major CpG DNAs ever developed

| Class | Name (sequence No) | Sequence *) | Subject |
|---|---|---|---|
| C | ODN2395 (17) | 5'-tcgtcgttttcggcgcgcgccg-3' | Human, mouse |

*) Capital letters represent a phosphodiester sugar backbone, and small letters represent a phosphorothioate sugar backbone; however, all the letters in the sequence listing are written by small letters, and the underline represents a palindrome sequence.

CITATION LIST

Patent Literature

PATENT LITERATURE 1: JP-A-2008-516634

Non-Patent Literature

NON-PATENT LITERATURE 1: Klein et al. Higher order structure of short immunostimulatory oligonucleotides studies by atomic force microscopy. Ultramicroscopy, 110: 689-693 (2010)
NON-PATENT LITERATURE 2: Krug et al. Identification of CpG oligonucleotide sequences with high induction of IFN-alpha/beta in plasmacytoid dendritic cells. Eur. J. Immunol. 31: 2154-2163 (2001)
NON-PATENT LITERATURE 3: Hartmann et al. Delineation of a CpG phosphorothioate oligodeoxynucleotide for activating primate immune responses in vitro and in vivo. J. Immunol. 164: 1617-1624 (2000)
NON-PATENT LITERATURE 4: Gungor B., Yagci F C., Tincer G., Bayyurt B., Alpdundar E., Yildiz S., Ozcan M., Gurcel I., Gurcel M. CpG ODN nanorings induce IFNα from plasmacytoid dendritic cells and demonstrate potent vaccine adjuvant activity. Science Translational Medicine 6, 235ra61 (2014)
NON-PATENT LITERATURE 5: Poeck et al. Plasmacytoid dendritic cells, antigen, and CpG-C license human B cells for plasma cell differentiation and immunoglobulin production in the absence of T cells help. Blood, 103: 3058-3064 (2004)

SUMMARY OF INVENTION

Technical Problem

In these prior art CpG ODNs, sugar backbone of the ODN is entirely or partially modified to become a phosphorothioate, in other words, any oxygen atoms of the phosphate group of the nucleotide composing the ODN are substituted by sulfur atoms. The ODN having a phosphorothioated sugar backbone is resistant to the deoxyribonuclease in the body, and shows a higher cellular uptake efficiency in comparison with the ODN composed entirely of a phosphodiester sugar backbone. However, it is pointed out that the ODN having a phosphorothioated sugar backbone nonspecifically bonds to proteins, and thus can cause side effects.

In addition, the CpG-A ODN has a higher-order structure as described above, but the structure contains various higher-order structures which are spontaneously generated during the course of synthesis. It is nearly impossible to industrially control the structure so as to form a specific higher-order structure, or to specify a higher-order structure which exhibits high IFN-inducing effect, thereby inhibiting a clinical application of the CpG-A ODN. The above-described Non-Patent Literature 4 suggests the preparation of a homogeneous nanocyclic structure by combination of the CpG-B with a cationic peptide, but there is little flexibility in the design because the number of bases of the ODN and the proportion to the carrier are limited.

Accordingly, the present invention is intended to provide an industrial-applicable immunostimulating oligonucleotide possessing excellent type-I IFN inducing activity even if it is not phosphorothioated.

Solution to Problem

Various studies were carried out for achieving the above-described problem, and it was surprisingly found that a linear double-stranded ODN, which contains CpG and is not phosphorothioated, is recognized by TLR9 and induces type-I IFN by forming a linear double-stranded ODN from the single-stranded ODNs, and combining the double-stranded ODN with a carrier, and thus the present invention has been accomplished. More specifically, the present invention is as follows:

[1] A linear double-stranded oligonucleotide containing 10 to 100 base pairs, each of the single-stranded oligonucleotides composing the double strand containing 2 to 20 cytosine-guanine sequences (CpG) mediated by phosphodiester, and 90% or more of the bonds between the nucleotides of the single-stranded oligonucleotides being phosphodiester bonds.

[2] The double-stranded oligonucleotide of [1], wherein the single-stranded oligonucleotides contain no palindrome sequence.

[3] The double-stranded oligonucleotide of [1] or [2], wherein all the bonds between the nucleotides of the single-stranded oligonucleotides are phosphodiester bonds.

[4] The double-stranded oligonucleotide of any one of [1] to [3], wherein the single-stranded oligonucleotide has either of the following base sequence or the sequence wherein one to three bases other than CpG are deleted, substituted, or added:

(SEQ ID NO. 1)
5'-TCGTCGTTTTGTCGTTTTGTCGTT-3'

(SEQ ID NO. 2)
5'-TCGTCGTTTTGTCGTTTTGTCGTTTCGTCGTTTTGTCGTTTTGTCGTT-3'

(SEQ ID NO. 3)
5'-TCGTCGTTTTGTCGTTTTGTCGTTTCGTCGTTTTGTCGTTTTGTCGTTTCGTCGTTTTGTCGTTTTGTCGTT-3'

(SEQ ID NO. 4)
5'-ATCGACTCTCGAGCGTTCTC-3'.

[5] An immunostimulating oligonucleotide complex comprising a carrier, and the double-stranded oligonucleotide of any one of [1] to [4] combined with the carrier.

[6] The immunostimulating oligonucleotide complex of [5], wherein the carrier is selected from a liposome, a polymer compound, and an inorganic compound.

[7] The immunostimulating oligonucleotide complex of [5] or [6], wherein the average particle size is 100 nm or more, preferably 250 nm or more, and more preferably 700 nm or more.

[8] The immunostimulating oligonucleotide complex of claim [5] or [6], wherein the weight ratio between the double-stranded oligonucleotide and the carrier is from 0.05:1 to 10:1, preferably from 0.1:1 to 10:1, and more preferably from 0.15:1 to 10:1.

[9] A vaccine adjuvant comprising the immunostimulating oligonucleotide complex of any one of [5] to [8].

[10] A method for preventing infection of mammals containing human, birds, or fishes, comprising administering sequentially or concurrently a detoxified or attenuated antigen derived from the pathogen causing the infection, and the immunostimulating oligonucleotide complex of any one of [5] to [8], thereby promoting production of the antibody against the pathogen in the body, and acquiring immunity against the infection.

[11] Use of the immunostimulating oligonucleotide complex of any one of [5] to [8] in the production of a vaccine for prevention of infection of mammals containing human, birds, or fishes.

[12] Use of the immunostimulating oligonucleotide complex of any one of [5] to [8] for prevention of infection of mammals containing human, birds, or fishes.

[13] A method for treatment or prevention of cancer, comprising treating or preventing cancer by administering a cancer antigen or its part and the immunostimulating oligonucleotide complex of any one of [5] to [8] continuously or simultaneously, thereby inducing the cytotoxic T cells (CTL) against the cancer antigen in the body, and allowing the CTLs to attack the cancer cells presenting the cancer antigen.

[14] Use of the immunostimulating oligonucleotide complex of any one of [5] to [8] in the production of a vaccine for treatment or prevention of cancer.

[15] Use of the immunostimulating oligonucleotide complex of any one of [5] to [8] for treating or preventing cancer.

[16] A pharmaceutical composition for treatment or prevention of an allergy, comprising the immunostimulating oligonucleotide complex of any one of [5] to [8].

[17] The pharmaceutical composition of [16], which further comprises an allergen or its portion.

[18] A method for treatment or prevention of an allergy, comprising treating or preventing an allergy by administering the immunostimulating oligonucleotide complex of any one of [5] to [8], thereby making the allergen-specific helper 1T (Th1) cells more active than the helper 2T (Th2) cells.

[19] The method of claim [18], which further comprises administering an allergen or its part concurrently or sequentially with the immunostimulating oligonucleotide complex.

[20] Use of the immunostimulating oligonucleotide complex of any one of [5] to [8] in the production of a medicine for treatment or prevention of an allergy.

[21] Use of the immunostimulating oligonucleotide complex of any one of [5] to [8] for treatment or prevention of an allergy.

Advantageous Effects of Invention

The double-stranded oligonucleotide of the present invention is free from the fear of side effects, because 90% or more of the bonds between the nucleotides are phosphodiester bonds and substantially free of phosphorothioate bonds. In addition, the formation of a complex is easy, the complex to be obtained has a controlled structure and size, and thus is expected to be used as an adjuvant. The complex is recognized by TLR9s of the antigen presenting cells, induces mainly the type-I IFN, and the amount of induction is significantly higher than the case where the CpG-B ODN is supported by the same carrier in the same manner.

DETAILED DESCRIPTION OF THE PREFERRED EMBODIMENTS

<Double-Stranded Oligonucleotide>

Figure 1:
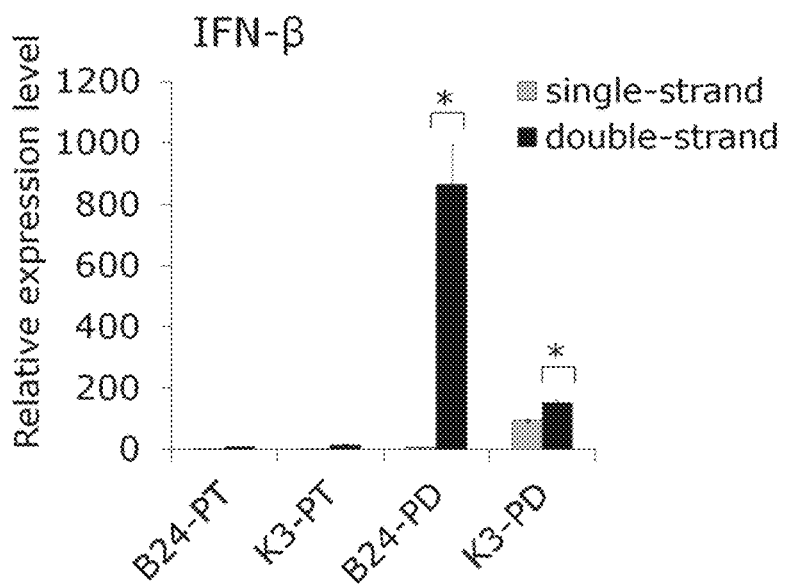
FIG. 1 is a graph showing the induction of IFN-β (relative expression amount) from the mouse macrophage-like cells shown in Example 1. The B24-PD and Lipofectamine 2000, i.e., the CpG ODN complex of the present invention, exhibited high IFN-β inducing potency in the form of a double-strand. *, $p<0.05$

In the present invention, "oligonucleotide" is an oligodeoxynucleotide (ODN), and is composed of a plurality of constitutional units composed of a base selected from adenine (A), guanine (G), cytosine (C), and thymine (T) bonded to phosphoric acid via deoxyribose.

The double-stranded CpG ODN of the present invention contains 10 to 100 base pairs, preferably 20 to 80 base pairs. The single-stranded CpG ODNs composing the double strand may have different base lengths, or may not have completely complementary base sequences. It is preferred that at least three bases before and after the CpG and CpG be complementary. The single-stranded CpG ODNs preferably have 80% or more, more preferably 90% or more complementarity. It is most preferred that the single-stranded CpG ODNs have the same base length, 100% complementarity, and form a double strand at the 3' and 5' terminals.

The double-stranded CpG ODN is linear. Typical examples of the linear structure include a double-helical structure whose center line is linear. However, in the present invention, "linear" includes a wide range of structures excluding a cyclic structure wherein both ends of the center line of the double helical structure are closed, for example, a large loop structure formed by linking of a noncomplementary sequence to a double-stranded cyclic structure such as plasmid DNA and a single-stranded DNA, and a block structure such as a tetramer structure of CpG-A ODN. A portion or an end of the linear structure may contain a linear or small looped part composed of about several to ten base lengths which does not form a double strand.

The single-stranded CpG ODN contains 2 to 20, preferably 4 or more, more preferably 6 or more cytosine-guanine sequences (CpGs) which are bonded via phosphodiester. The nucleotide other than CpG may be freely selected. The position of the CpG in the base sequence is not particularly limited, but is preferably apart from the 3' and 5' terminals by one nucleotide or more. In addition, the CpGs are preferably separated by one or more nucleotides.

90% or more, preferably 95% or more, and most preferably 100% of all the bonds between the nucleotides in the single-stranded CpG ODNs are phosphodiester bonds. The phosphodiester bonds may contain, for example, phosphorothioate bonds formed by substituting the above-described oxygen atoms in the phosphate groups of the nucleotides with sulfur atoms, 2'-O,4'-C-methano-bridged nucleic acid (2',4'-BNA) formed by modification of the sugar of the nucleotide, or its derivative, a 3'-amino-BNA, 5'-amino-BNA structure at a proportion of 10% or less of the total number of bonds.

The single-stranded CpG ODNs induce type-I IFN though not containing a palindrome sequence, and preferably contain no palindrome sequence.

A preferred example of the single-stranded CpG ODN in the present invention has either of the following base sequences or the sequences wherein one to three bases other than CpG are deleted, substituted, or added:

(SEQ ID NO. 1)
5'-TCGTCGTTTTGTCGTTTTGTCGTT-3'

(SEQ ID NO. 2)
5'-TCGTCGTTTTGTCGTTTTGTCGTTTCGTCGTTTTGTCGTTTTGTCGT

T-3'

(SEQ ID NO. 3)
5'-

TCGTCGTTTTGTCGTTTTGTCGTTTCGTCGTTTTGTCGTTTTGTCGTTTC

GTCGTTTTGTCGTTTTGTCGTT-3'

(SEQ ID NO. 4)
5'-ATCGACTCTCGAGCGTTCTC-3'

In the above-described sequence, all the bonds between the nucleotides are phosphodiester bonds, but as described above, some of them may be phosphorothioate bonds or the like. In addition, other single-stranded CpG ODN has a sequence complementary to the above-described sequence. As explained regarding Table 1, in the present description, the bases represented by capital letters are bonded by phosphodiester.

The linear double-stranded CpG ODN can be prepared by synthesizing each single-stranded CpG ODN by a nucleic acid synthesizing apparatus separately, mixing them in equimolar amounts in a buffer, heating at about 88 to 98° C. for about 5 to 30 minutes, and then gradually decreasing the temperature at about 0.1 to 2° C./minute. At that time, these single-stranded CpG ODNs have base sequences complementary to each other, and the complementary bases of these single-stranded CpG ODNs form hydrogen bonds to produce a double-stranded CpG ODN.

Another method for obtaining a linear double-stranded CpG ODN is a method of amplifying the region containing CpG by PCR, using the genome ODN of a bacterium or virus as the template. Alternatively, a cyclic plasmid ODN is amplified in the host cells and the recovered cyclic plasmid is cleaved by a restriction enzyme to obtain the linear double-stranded CpG ODN.

<Immunostimulating Oligonucleotide Complex>

A second aspect of the present invention is an immunostimulating oligonucleotide complex formed by combining a double-stranded CpG ODN, which has been prepared as described above, and a physiologically acceptable carrier. The combination enhances the type-I IFN inducing potency. The "physiologically acceptable carrier" means a substance which will not damage and inhibit the cells, tissues, or organs in the body to achieve the object of the invention. Examples of the carrier include polymer compounds, emulsions, liposomes, inorganic compound particles, metal particles, metal oxide particles, carbon particles, and modified products thereof, and cationic ones are preferred.

Examples of the polymer compound include cationic polymers such as polyethyleneimine, chitosan, polyricin, LL-37, and Tat. These cationic polymers electrostatically combine to the double-stranded CpG ODN of the present invention. Alternatively, DNA may be included in poly (lactic-co-glycolic acid) (PLGA), which is a biodegradable polymer. Multimers such as dendrimers may be usable as carriers.

Examples of the emulsion include water/oil emulsions and water/oil/water emulsions, and the double-stranded CpG ODN may be included in the aqueous phase. Examples of the liposome include a liposome composed of a lipid bilayer containing a double-stranded CpG ODN, and a cationic liposome, such as one containing a long-chain alkyl group and an amino group or an ammonium group, electrostatically bonded to a double-stranded CpG ODN.

Examples of the inorganic compound particles include calcium phosphate particles, hydroxyapatite particles, carbonate apatite particles, and silica nanoparticles. Examples of the metal particles include gold particles, silver particles, platinum particles, and silicon nanoparticles. Examples of the metal oxide particles include zinc oxide particles, titanium dioxide particles, alumina particles, and zirconia particles. Examples of the carbon particles include fullerene, carbon nanotubes, and carbon nanohorns.

The size of these carrier particles is not particularly limited, but is preferably from 10 nm to 1 and more preferably from 100 to 800 nm in terms of the length or the average of the longest diameter ($D_{50}$). The particle shape is not particularly limited, and may be spherical, flake, or columnar.

Among the above-described carriers, cationic liposomes and inorganic compound particles are preferred, for example, cationic liposomes containing a long-chain alkyl group and an amino group or an ammonium group, for example, Lipofectamine (trademark), DOTAP(N-[1-(2,3-Dioleoyloxy)propyl]-N,N,N-trimethylammonium methylsulfate), DMTAP (dimyristoyltrimethylammonium propane), DOAB (dimethyldioctadecylammonium (bromide salt)), DODAP (1,2-dioleoyl-3-dimethylammonium-propane), DC-CHOL (3b-[N—(N',N'-dimethylaminoethane)-caramoyl] cholesterol hycrochloride), DOSPA (N-[2-[(1,5,10,14-Tetraazatetradecane-1-yl)carbonylamino]ethyl]-N,N-dimethyl-2,3-bis(oleoyloxy)-1-propanaminium), or mixtures with DOPE (1,2-dioleoyl-sn-glycero-3-phosphoethanolamin) having no electric charge (for example, DOSPA/DOPE (3:1 wt/wt)), and the inorganic compound is preferably calcium phosphate or DEAE dextran. Alternatively, their mixtures are preferred.

The method for combining the double-stranded CpG ODN of the present invention with any of these carriers is not particularly limited. Electrostatic bonds between the double-stranded CpG ODN and a carrier whose surface is positively charged can be formed electrostatically by mixing them in an appropriate buffer. The double-stranded CpG ODN adsorbs to calcium phosphate particles, hydroxyapatite particles, carbonate apatite particles, fullerene, carbon nanotubes, and carbon nanohorns. When a carrier whose surface is not positively charged is used, the surface of the carrier particle is modified with a positively charged substance such as polyethyleneimine, chitosan, or polyricin to electrostatically bond the double-stranded CpG ODN, or maleimide groups are introduced to the carrier particle surface, and thiol groups are introduced to the terminals of the linear double-stranded CpG ODN, thereby forming covalent bonds.

The weight ratio between the double-stranded CpG ODN and the carrier is preferably adjusted as appropriate according to the base chain length of the double-stranded CpG ODN, the properties of the carrier, and the antigen to be used in combination. The weight ratio between the double-stranded CpG ODN and the carrier is typically from 0.05:1 to 10:1.

The effect of the oligonucleotide complex can be measured by administering it to the cells having TLR9, for example, human and mouse plasma cell-like dendritic cells, mouse macrophage, or mouse conventional dendritic cells, and then determining the expression amounts of type-I IFN and inflammatory cytokine genes, or determining the secretion amounts of type-I IFN and inflammatory cytokine. For example, the gene expression amount and secretion amount can be determined by, for example, the real-time quantitative PCR and ELISA method, respectively.

The complex is expected to exhibit adjuvant effect by being administered together with an antigen or allergen. The complex may be administered in the form of a mixture with a free antigen or allergen. Alternatively, a compounding of an antigen or allergen with the complex supported on the same carrier may be administered, or a complex of an antigen or allergen, which has been bonded to a double-stranded CpG ODN, may be supported on a carrier, and administered. Further alternatively, an antigen or allergen and the complex are supported on separate carriers, and they may be mixed and administered.

The method for combining an antigen or allergen with a carrier is not particularly limited; for example, an antigen or allergen is contained in the hollow of a cationic liposome, and a linear double-stranded CpG ODN is electrostatically bonded to the surface of the cationic liposome; a linear double-stranded CpG ODN and an antigen or allergen are concurrently adsorbed to the surface of calcium phosphate particles, hydroxyapatite particles, or carbonate apatite particles.

Alternatively, a linear double-stranded CpG ODN and an antigen or allergen are previously mixed with the raw material liquid for preparing calcium phosphate particles, hydroxyapatite particles, or carbonate apatite particles, thereby the linear double-stranded CpG ODN and antigen or allergen are concurrently contained in these particles. When an antigen or allergen is previously bonded to a linear double-stranded CpG ODN before being supported on a carrier, the ends of the linear double-stranded CpG ODN are modified by thiol groups, while maleimide groups are introduced to the amino groups of the antigen or allergen, and the thiol groups and maleimide groups are combined by covalent bonds.

Examples of the antigen include hand-foot-mouth disease virus antigen, dengue fever virus antigen, and West Nile fever virus antigen. Examples of the allergen include the cedar pollen allergen, ragweed allergen, rice allergen, and mite allergen. Other examples include the cancer cell antigen.

The vaccine herein means the drugs used for prevention of infections. A detoxified or attenuated antigen is administered, thereby promoting production of the antibody against the pathogen in the body, and acquiring immunity against the infection. Examples of the living virus vaccines in practical use made from attenuated microorganisms or viruses include, not specifically limited to, BCG, oral living polio (OPV) vaccine, lymph (smallpox), measles vaccine, rubella vaccine, measles-rubella vaccine (MR vaccine), epidemic parotitis (mumps) vaccine, pox vaccine, yellow fever vaccine, rotavirus vaccine, and herpes zoster vaccine. Examples of the inactivated vaccines in practical use containing viruses, bacteria, *rickettsia* killed by chemical treatment, or cultures of their antigen parts alone include influenza virus vaccine, pneumonia coccus vaccine, rabies vaccine, cholera vaccine, DT vaccine (diphtheria-tetanus vaccine), DPT vaccine (diphtheria-pertussis-tetanus vaccine), DPT-IPV vaccine (diphtheria-pertussis-tetanus-inactivated polio vaccine), encephalitis vaccine, and pertussis vaccine.

The cancer vaccine means the vaccine used for the purpose of treatment or prevention of cancer. The antigen (cancer antigen) used herein is the full length or a part (peptide) of the antigen protein which is not expressed or slightly expressed in healthy cells, and excessively expressed in cancer cells. Examples include, but not particularly limited to, MAGE in malignant melanoma, HER2/neu in breast cancer, CEA in large intestine cancer, WT1 in various kinds of leukemia and cancer, and NY-ESO-1 in malignant melanoma, esophagus cancer, stomach cancer, and ovarium cancer. Cytotoxic T cells (CTLs) recognize these cancer antigen proteins (or their decomposed peptides) in the body, and attack the cancer cells (cellular immunity). The cancer vaccine therapy treats cancer by artificially administering a cancer antigen (peptide) to induce specific CTLs (proliferation and differentiation).

The cancer vaccine also includes the vaccines for inhibiting infection with carcinogenic virus. Type B hepatitis virus vaccine (which causes hepatic carcinoma through hepatocirrhosis) and human papilloma virus (which causes cervical cancer) are practically used.

In the patients with pollen allergy or house dust allergy, the helper 2T (Th2) pathways specific to these allergens are dominant over the helper 1T (Th1) pathways. More specifically, it is one of treatment strategies to activate the allergen-specific Th1 pathway, thereby making it dominant over the Th2 pathway. In mice, the IgG2a/IgG1 ratio is the index of the Th1/Th2 ratio, but in human, the IgG4/IgG1 ratio may be the index of the Th1/Th2 ratio.

The subject of the present application include mammals containing human (primates such as monkeys; companion animals such as dogs and cats; livestock such as horses, pigs, cattle, goats, and sheep; and experimental animals such as rats and mice), birds (wild birds or fowls such as chickens and turkeys) or fishes (aquaculture species: for example, freshwaters such as sweetfishes and whitefishes, sea fishes such as yellowtails and greater yellowtails), but not particularly limited as long as TLR9 is expressed therein.

EXAMPLES

The present invention is explained by the following examples, but the present invention will not be limited to these examples.

<Preparation of Single-Stranded CpG ODN and Linear Double-Stranded CpG ODN>

Single-stranded CpG ODNs having the sequences shown in Table 2, and single-stranded ODNs having the sequences complementary to these base sequences were synthesized, and hybridized to prepare double-stranded CpG ODNs. The hybridization was carried out as follows: any of the single-stranded CpG ODNs of the SEQ ID Nos. shown in Table 2 was mixed with its complementary single-stranded CpG ODN in a TES buffer (10 mM Tris-HCl pH 8.0, 1 mM EDTA and 0.25 mM NaCl) at an equimolar ratio, incubated at 95° C. for 10 minutes, and then the temperature was decreased to 30° C. over a period of 60 minutes. As a result of the hybridization, a complete linear double-stranded ODN was obtained.

For comparison, the single-stranded and double-stranded ODNs of SEQ ID Nos. shown in Table 3, and the single-stranded and double-stranded ODNs of SEQ ID Nos. shown in Table 4 for reference were prepared in the same procedure as described above. The B24-PT (SEQ ID NO. 5) in Table 3 is the same as the ODN2006 in Table 1.

TABLE 2

SEQ ID NO. 1
B24-PD (single-stranded CpG ODN of 24 bases in length wherein all nucleotides are phosphodiester)
5'-TCGTCGTTTTGTCGTTTTGTCGTT-3'

SEQ ID NO. 2
B48-PD (single-stranded CpG ODN of 48 bases in length wherein all nucleotides are phosphodiester)
5'-TCGTCGTTTTGTCGTTTTGTCGTTTCGTCGTTTTGTCGTTTTGTCGTT-3'

SEQ ID NO. 3
B72-PD (single-stranded CpG ODN of 72 bases in length wherein all nucleotides are phosphodiester)
5'-TCGTCGTTTTGTCGTTTTGTCGTTTCGTCGTTTTGTCGTTTTGTCGTTTCGTCGTTTTGTCGTTTTGTCGTT-3'

SEQ ID NO. 4
K3-PD (single-stranded CpG ODN of 20 bases in length wherein all nucleotides are phosphodiester)
5'-ATCGACTCTCGAGCGTTCTC-3'

TABLE 3

SEQ ID NO. 5
B24-PT (single-stranded CpG ODN of 24 bases in length wherein all nucleotides are phosphorothioate)
5'-tcgtcgttttgtcgttttgtcgtt-3'

SEQ ID NO. 6
B48-PT (single-stranded CpG ODN of 48 bases in length wherein all nucleotides are phosphorothioate)
5'-tcgtcgttttgtcgttttgtcgtttcgtcgttttgtcgttttgtcgtt-3'

SEQ ID NO. 7
B72-PT (single-stranded CpG ODN of 72 bases in length wherein all nucleotides are phosphorothioate)
5'-tcgtcgttttgtcgttttgtcgtttcgtcgttttgtcgttttgtcgtttcgtcgttttgtcgttttgtcgtt-3'

SEQ ID NO. 8
K3-PT (single stranded CpG ODN of 20 bases in length Wherein all nucleotides are phosphorothioate)
5'-atcgactctcgagcgttctc-3'

TABLE 4

SEQ ID NO. 9
CpG-free 24-PD (CpG-free single-stranded ODN of 24 bases in length wherein all nucleotides are phosphodiester)
5'-TCAGAGAGTTAGAGAGTTAGAGAG-3'

TABLE 4-continued

SEQ ID NO. 10
CpG-free 48-PD (CpG-free singe-stranded ODN of 48 bases in length wherein all nucleotides are phosphodiester)
5'-TCAGAGAGTTAGAGAGTTAGACAGTCAGAGAGTTAGAGAGTTAGAGAG-3'

SEQ ID NO. 11
CpG-free 72-PD (CpG-free singie-stranded ODN of 72 bases in length wherein ail nucleotides are phosphodiester)
5'-TCAGAGAGTTAGAGAGTTAGAGAGTCAGAGAGTTAGAGAGTTAGAGAGTCAGAGAGTTAGAGAGTTAGAGAG-3'

Example 1

B24-PT (SEQ ID NO. 5), K3-PT (SEQ ID NO. 8), B24-PD (SEQ ID NO. 1), K3-PD (SEQ ID NO. 4), CpG-free 24-PD (SEQ ID NO. 9) in the form of single-stranded ODNs, and their linear double-stranded ODNs were individually mixed with Lipofectamine (registered trademark) 2000 (Life Technologies) which is a cationic liposome, at a weight ratio of 1:1, and electrostatically combined.

RAW264.7, which is a cell line of mouse macrophage, was used as the TLR9-containing cells. The cell line was seeded on an Eagle minimum essential culture medium (MEM) at a density of $3.3 \times 10^5$ cells/ml. After 24 hours, the complexes of B24-PT, K3-PT, B24-PD, K3-PD, CpG-free 24-PD, and their double-stranded ODNs with Lipofectamine 2000 were added to make the concentration of Lipofectamine 2000 5 μg/ml. More specifically, the ODN (B24-PT, K3-PT, B24-PD, K3-PD, and their double-stranded DNAs) bonded to Lipofectamine 2000 were added at a concentration of 5 μg/ml. After 6 hours, the cells were collected, all the RNAs were extracted by ISOGEN (Nippon Gene Co., Ltd.), and then cDNA was synthesized by a reverse transcriptase (TaKaRa Bio Inc.). Using this cDNA as the template, the expression amount of the IFN-β gene was measured by real-time quantitative PCR. The expression amount of the IFN-β gene was normalized by the expression amount of the GAPDH gene. The primer sequence for the measurement of the IFN-β expression amount by real-time quantitative PCR was as follows: forward, 5'-GGTCCGAGCAGAGATCTTCA-3' (SEQ ID NO. 29); reverse, 5'-TCACTACCAGTCCCAGAGTCC-3' (SEQ ID NO. 30). The primer sequence for the measurement of the GAPDH gene expression amount was as follows: forward, 5'-GTGGACCTCATGGCCTACAT-3' (SEQ ID NO. 31); and reverse, 5'-TGTGAGGGAGATGCTCAGTG-3' (SEQ ID NO. 32).

As shown in FIG. 1, the complexes of the B24-PT and K3-PT with Lipofectamine 2000 did not induce IFN-β, neither the single strand nor double strand. On the other hand, in the B24-PD and K3-PD, markedly high IFN-β was induced by their double strands. In addition, the double-stranded B24-PD showed higher IFN-β inducing potency than the double-stranded K3-PD.

Example 2

As described above, in Example 1, the complex of the double-stranded B24-PD with Lipofectamine 2000 showed high the induction of IFN-β from the RAW264.7 cells via TLR9. The double-stranded B24-PD has a length of 24 base pairs, and contains four CpGs in each chain. The double-stranded B48-PD composed of two double-stranded B24-PDs has a length of 48 base pairs, and contains 8 CpGs in each chain. In addition, the double-stranded B72-PD composed of three double-stranded B24-PDs has a length of 72 base pairs, and contains 12 CpGs in each chain. These double-stranded CpG ODNs were bonded to Lipofectamine 2000 in the same manner as in Example 1, and the RAW264.7 cells were irritated.

Figure 2:
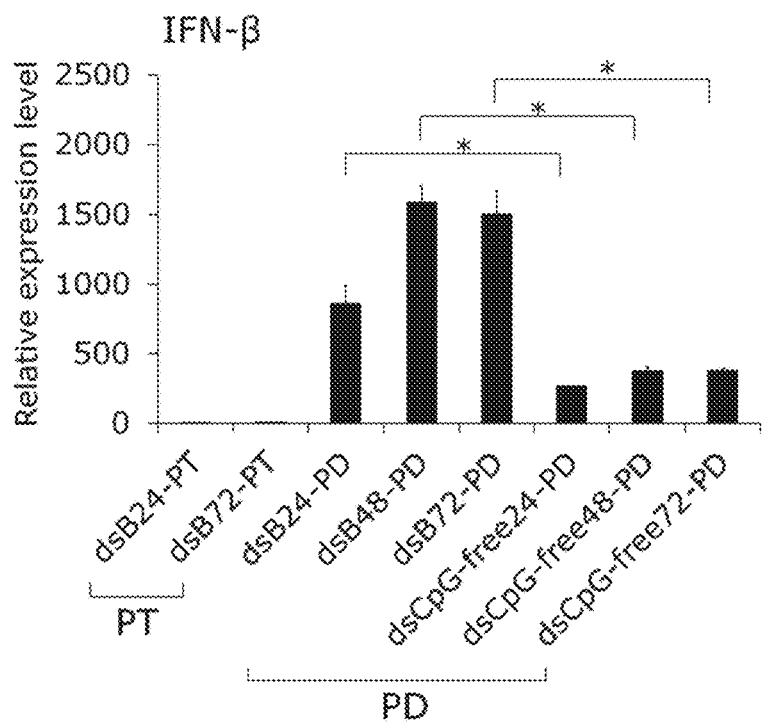
FIG. 2 is a graph showing the induction of IFN-β from the mouse macrophage-like cells shown in Example 2. The double-stranded CpG ODN complex of the present invention exhibited high IFN-β inducing potency when the number of base pairs is 48 or more. *, $p<0.05$

The results are shown in FIG. 2. In FIG. 2, "ds" represents a double strand, "PT" represents a phosphorothioated sugar backbone, and "PD" means a phosphodiester sugar backbone. As shown in FIG. 2, the amount of induced IFN-β by the double-stranded B48-PD was markedly higher than that by the double-stranded B24-PD. However, the amount of induced IFN-β by the double-stranded B72-PD was not different from that by the double-stranded B48-PD. These facts suggest that the high amount of induced IFN-β and the CpG sequence number are not in simple proportional relationship, and there is an optimum number. On the other hand, the double-stranded phosphorothioated B72-PT scarcely induced IFN-β. This fact means that the double-stranded phosphorothioated CpG ODN will not improve the IFN-β inducing potency, even if the number of CpGs is increased.

The RAW264.7 cells have cytosolic DNA receptors such as TLR9, DAI, IFI16, DDX41, and cGAS. The cytosolic DNA receptors recognize double-stranded DNAs irrespective of the base sequences, and induce type-I IFN. Accordingly, the IFN-β by the double-stranded B24-PD, double-stranded B48-PD, and double-stranded B72-PD is likely induced by both of the TLR9 and cytosolic DNA receptor. Therefore, the amounts of induced IFN-β from the double-stranded CpG-free 24-PD, double-stranded CpG-free 48-PD, and CpG-free double-stranded B72-PD having lengths of 24 base pairs, 48 base pairs, and 72 base pairs, respectively, were studied.

As shown in FIG. 2, the amounts of IFN-β induced from the double-stranded CpG-free 24-PD, double-stranded CpG-free 48-PD, and CpG-free double-stranded B72-PD having lengths of 24 base pairs, 48 base pairs, and 72 base pairs, respectively, were significantly lower than those from the double-stranded CpG-free 24-PD, double-stranded B48-PD, and double-stranded B72-PD. This fact indicates that the induction of IFN-β from the double-stranded CpG-free 24-PD, double-stranded B48-PD, and double-stranded B72-PD was mostly mediated by TLR9.

Example 3

Figure 3:
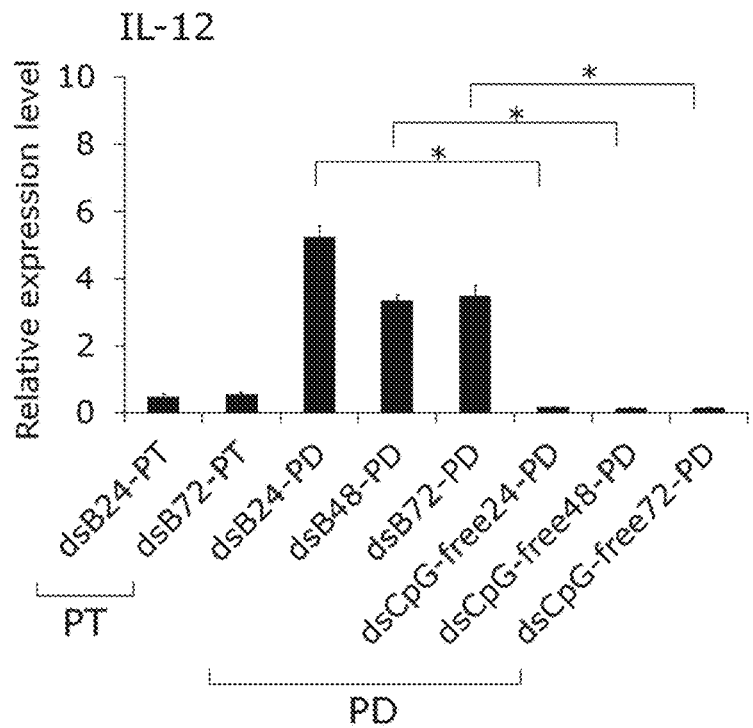
FIG. 3 is a graph showing the induction of IL-12 from the mouse macrophage-like cells shown in Example 3. The double-stranded CpG ODN complex of the present invention exhibited not only IFN-β inducing potency but also IL-12 inducing potency. *, $p<0.05$

The amount of induced IL-12, which is an inflammatory cytokine, was measured by real-time quantitative PCR under the same conditions as in Example 2. The primer sequence for measuring the amount of induced IL-12 was: forward, 5'-GAAAGGCTGGGTATCGG-3' (SEQ ID NO. 33); reverse, 5'-GGCTGTCCTCAAACTCAC-3' (SEQ ID NO. 34). As shown in FIG. 3, all the complexes of the double-stranded B24-PD, double-stranded B48-PD, and double-stranded B72-PD with Lipofectamine 2000 induced IL-12 from the RAW264.7 cells. Differently from IFN-β, the induced amount was higher for the double-stranded B24-PD than the double-stranded B48-PD and double-stranded B72-PD. These results indicate that the double-stranded CpG ODN complex of phosphodiester induces IL-12 as well as IFN-β.

Example 4

The amounts of induced IFN-β by the free double-stranded B72-PD and double-stranded B72-PD, which did not form a complex, and their complexes with Lipofectamine 2000 were compared. The complex of the double-stranded B72-PD with Lipofectamine 2000 was prepared in the same manner as in Example 1. The RAW264.7 cells were cultured in the same manner as in Example 1. The free double-stranded B72-PD not combined with Lipofectamine 2000 was added to the culture medium to make the concentration 50 μg/ml. This concentration was ten times the concentration of the double-stranded B72-PD combined with Lipofectamine 2000 (5 μg/ml).

Figure 4:
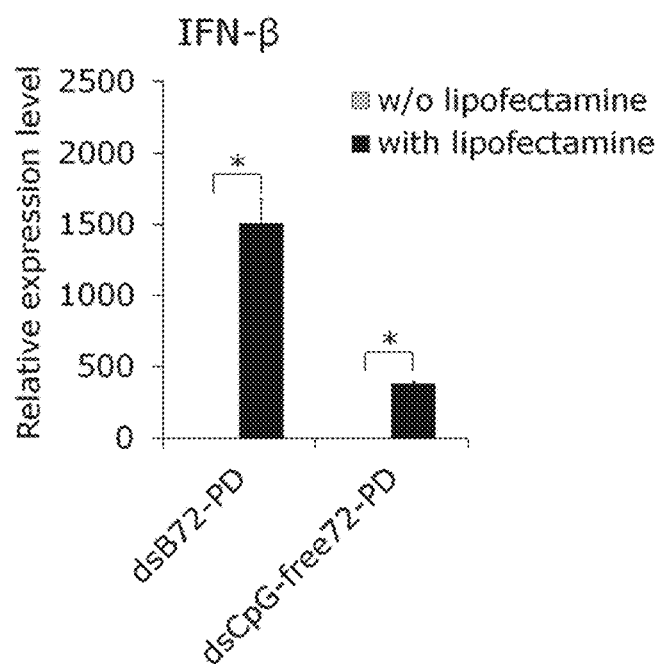
FIG. 4 shows the induction of IFN-β from the mouse macrophage-like cells shown in Example 4. It shows that the induction of IFN-β from the phosphodiester double-stranded linear CpG ODN of the present invention essentially required the compounding with a carrier. *, $p<0.05$

As shown in FIG. 4, the double-stranded B72-PD induced IFN-β only when combined with Lipofectamine 2000. This fact means that the combination is absolutely necessary for the induction of IFN-β by the double-stranded CpG ODN of phosphodiester.

Example 5

The double-stranded B72-PD and double-stranded CpG-free 72-PD were mixed with DOTAP (Roche Life Science), which is a cationic liposome, at a weight ratio of 1:6, thereby electrostatically bonding them together. The RAW264.7 cells were cultured in the same manner as in Example 1, and added into the culture medium to make the DOTAP concentration 30 μg/ml. More specifically, the concentration of the double-stranded B72-PD and double-stranded CpG-free 72-PD combined with DOTAP in the culture medium was 5 μg/ml. On the other hand, the free double-stranded B72-PD and double-stranded CpG-free 72-PD not combined with DOTAP were added to the culture medium to make their concentration 50 μg/ml. This concentration was ten times the concentration of the double-stranded B72-PD combined with DOTAP (5 μg/ml).

Figure 5:
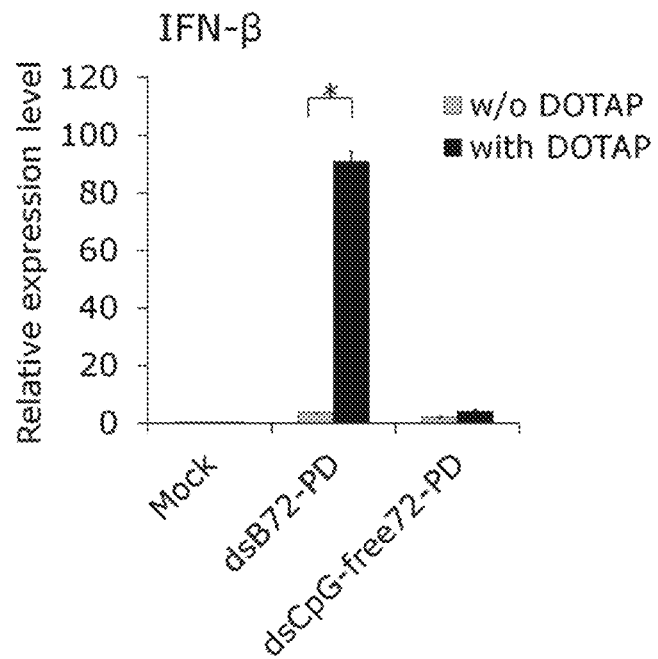
FIG. 5 shows the induction of IFN-β from the mouse macrophage-like cells shown in Example 5. It shows that the double-stranded CpG ODN complex of the present invention induced IFN-β along with a cationic liposome other than Lipofectamine 2000. *, $p<0.05$

As shown in FIG. 5, the double-stranded B72-PD combined with DOTAP also induced IFN-β. The fact that the double-stranded CpG-free 72-PD combined with DOTAP scarcely induced IFN-β indicates that the induction of IFN-β by the double-stranded B72-PD combined with DOTAP is mediated by TLR9, not by a cytosolic DNA receptor.

Figure 6:
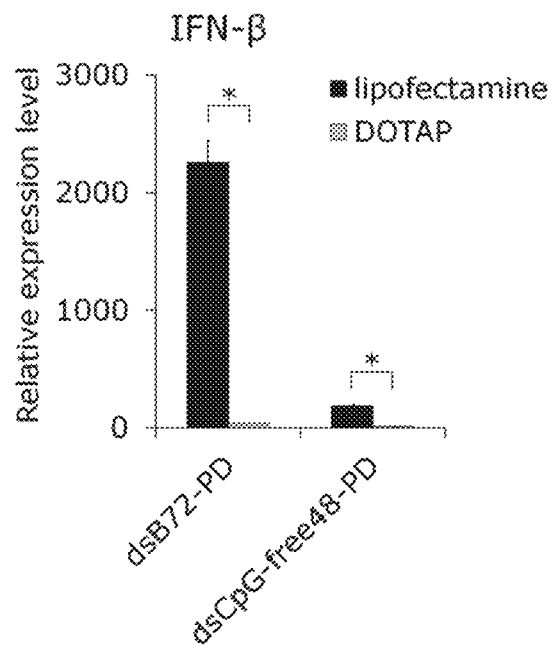
FIG. 6 shows the comparison of the amount of the induction of IFN-β between the complex with Lipofectamine 2000 shown in FIG. 4 and the complex with DOTAP shown in FIG. 5. The double-stranded CpG ODN of the present invention exhibited higher IFN-β inducing potency when combined with Lipofectamine 2000, than when combined with DOTAP. *, $p<0.05$

FIG. 6 shows the comparison of the amount of induced IFN-β by the complex of the double-stranded B72-PD with DOTAP shown in FIG. 5, and with Lipofectamine 2000 shown in FIG. 4. As shown in FIG. 6, the amount of induced IFN-β from the double-stranded B72-PD combined with DOTAP was significantly lower than the complex with Lipofectamine 2000. This fact indicates that the carrier for combining the double-stranded CpG ODN of phosphodiester markedly influences the induction of IFN-β.

Example 6

The single-stranded B72-PD, double-stranded B72-PD, and double-stranded CpG-free 72-PD were bonded to the surface of calcium phosphate particles, and the induction of IFN-β dependent on TLR9 from the RAW264.7 cells was examined. 17.52 μl of distilled water was added to 2.48 μl of 2 mol/l $CaCl_2$ solution to make the total amount 20 μl. 12.5 μl of the solution was added to 100 μl of 2× Hank's Balanced Salt Solution (Life Technologies), thus obtaining a calcium phosphate precipitate. The precipitate of calcium phosphate was composed of rod-shaped particles having a length of about 150 nm. Five μg portions of the single-stranded B72-PD, double-stranded B72-PD and double-stranded CpG-free 72-PD were separately adsorbed to the particles of the calcium phosphate thus obtained (about 11.6 μg). They were added to the RAW264.7 cells to make the ODN concentration 5 µg/ml, and the amount of induced IFN-β was measured after 6 hours.

Figure 7:
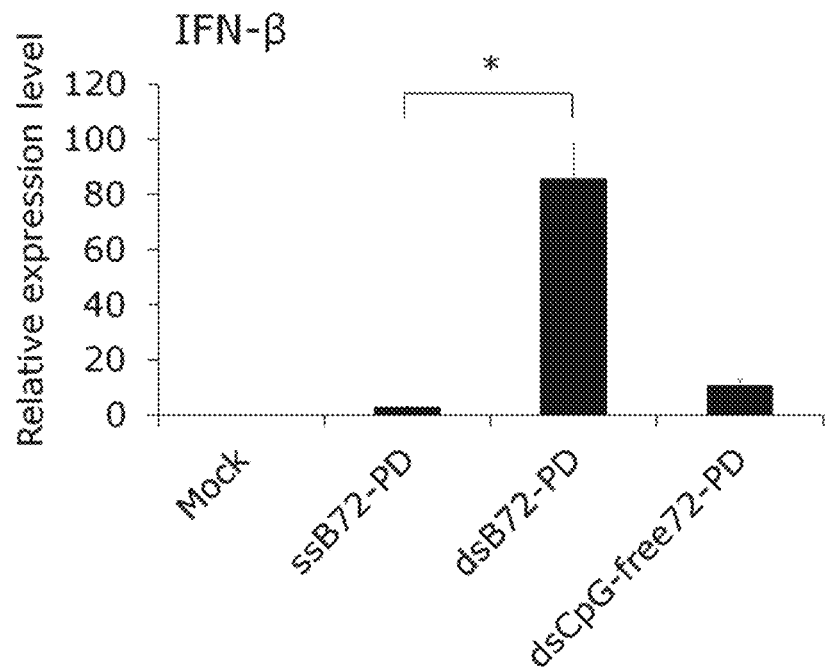
FIG. 7 shows the induction of IFN-β from mouse macrophage-like cells shown in Example 6. The double-stranded CpG ODN of the present invention exhibited high IFN-β inducing potency when combined with calcium phosphate particles. *, $p<0.05$

As shown in FIG. 7, the double-stranded B72-PD combined with calcium phosphate particles showed markedly high IFN-β inducing potency than the single-stranded B72-PD. In addition, the fact that the double-stranded CpG-free 72-PD combined with calcium phosphate particles scarcely induced IFN-β indicates that the induction of IFN-β by the double-stranded B72-PD combined with calcium phosphate particles is mediated by TLR9, not by a cytosolic DNA receptor. Furthermore, this result means that IFN-β is induced by the phosphodiester linear double-stranded CpG ODN bonded to particles other than cationic liposome.

Example 7

The human peripheral blood mononuclear cells (Cellular Technology Limited., OH, USA) purchased from Cellular Technology Limited (OH, USA) were collected by centrifugation, suspended in 800 µl of autoMACS Rincing Solution (Militenyi Biotech, Bergisch Gladbach, Germany), and then 200 µl of CD14 MicroBeads (Militenyi Biotech) was added, and incubated at 6° C. for 15 minutes. The Micro Beads were collected by centrifugation, suspended in 1000 µl of autoMACS Rincing Solution, and then the suspension was passed through a LS column (Militenyi Biotech) under a magnetic field (MidiMACS Separation Unit, Militenyi Biotech). The $CD14^+$ monocytes were recovered from the column. $CD304^+$ plasma cell-like dendritic cells and $CD20^+$ B cells were separately isolated from the column eluate using CD304 MicroBeads (Militenyi Biotech) and CD20 MicroBeads (Militenyi Biotech) in the same manner as described above. In addition, the proportions of the isolated B cells, plasma cell-like dendritic cells, and monocytes in the human peripheral blood mononuclear cells were 1.2 to 2.0%, 0.1 to 0.63%, and 12 to 20%, respectively.

The B cells and plasma cell-like dendritic cells isolated from the human peripheral blood mononuclear cells were seeded on 96-well flat-bottom plates at a density of $2\times10^4$ cells/well. These cells were cultured in media composed of 200 µl RPMI 1640 (Invitrogen, Life Technologies, CA, USA) mixed with 10% (v/v) FBS, 1 ml of L-glutamine, 100 U/ml of penicillin, and 100 µg/ml of streptomycin.

B24-PT, B72-PT, B72-PD, CpG-free 72-PD, and their double-stranded DNAs were combined with DOTAP in the same manner as in Example 5, and added concurrently with seeding of the plasma cell-like dendritic cells. After 48 hours, the amount of induced IFN-α was measured by IFN-α Enzyme-linked immunosorbent assay kit (IFN-α ELISA kit, Affymetrix, CA, USA).

Figure 8:
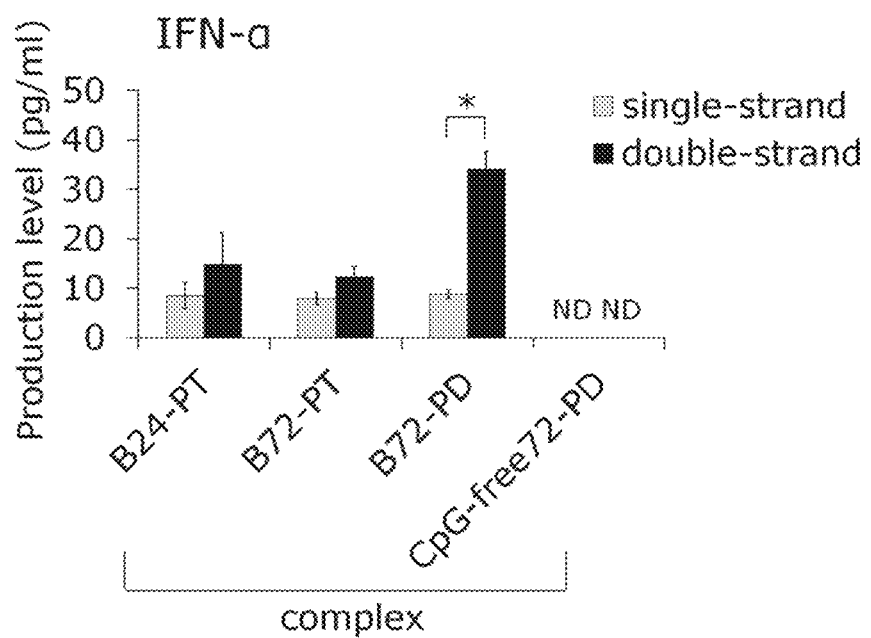
FIG. 8 shows the induction of IFN-α from the human plasma cell-like dendritic cells shown in Example 7. High IFN-α inducing potency was exhibited when the double-stranded CpG ODN of the present invention was combined with DOTAP. *, $p<0.05$

As shown in FIG. 8, the amounts of IFN-α induced by B24-PT and B72-PT did not markedly change even when they were in the form of double strands, but the amount of IFN-α induced by B72-PD was markedly higher when it was in the form of a double strand than in the form of a single strand. In addition the double-stranded CpG-free 72-PD did not induce IFN-α, which indicates that the IFN-α from the complex of the double-stranded B72-PD with DOTAP is dependent on TLR9.

In the next place, B24-PT, B72-PD, CpG-free 72-PD, and their double-stranded DNAs were combined with DOTAP in the same manner as in Example 1, and added concurrently with seeding of B cells. In addition, free B24-PT, B72-PD, CpG-free 72-PD, and their double-stranded DNAs not combined with DOTAP were added into the culture medium to make the concentration 50 µg/ml. After 48 hours, the amount of induced IL-6 was measured by IL-6 ELISA kit (Affymetrix).

Figure 9:
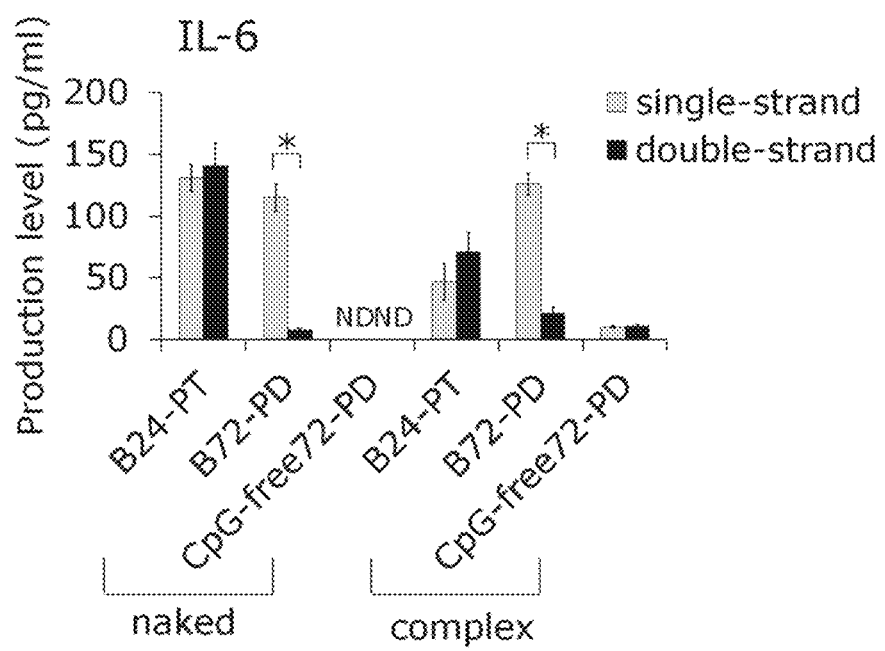
FIG. 9 shows the induction of IL-6 from the human B cells shown in Example 7. Both of the phosphodiester double-stranded linear CpG ODN in a free state and its complex with DOTAP induced lower amounts of IL-6 in comparison with the single strand. In addition, the amounts were lower than those by the single-stranded and double-stranded phosphorothioate CpG ODNs. *, $p<0.05$

As shown in FIG. 9, both of the free single-stranded B24-PT and the single-stranded B72-PD not combined with DOTAP induced IL-6. However, in the form of a double strand, the B24-PT induced IL-6, but the B24-PD did not induce IL-6. When combined with DOTAP, the single-stranded B72-PD induced IL-6, but the double-stranded B72-PD did not induce IL-6. On the other hand, the complex of the double-stranded B24-PT and DOTAP induced IL-6. The fact that the double-stranded B72-PD did not induce inflammatory cytokine such as IL-6 suggests that the double-stranded CpG ODN of phosphodiester has small side effects.

B24-PT, B72-PT, B72-PD, CpG-free 72-PD, and their double-stranded DNAs were combined with DOTAP in the same manner as in Example 1, and added concurrently with seeding of monocytes. After 48 hours, the amount of induced IFN-α was measured.

Figure 10:
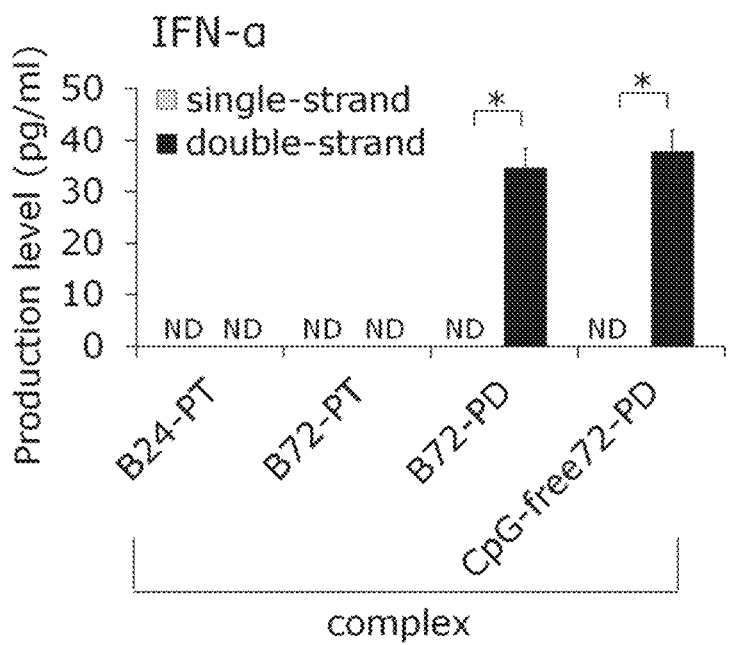
FIG. 10 shows the induction of IFN-α from the human monocytes shown in Example 7. The double-stranded CpG ODN complex of the present invention was recognized by the cytosolic DNA receptor, and induced IFN-α. *, $p<0.05$

As shown in FIG. 10, the double-stranded B72-PD induced IFN-α. The facts that human monocytes do not have TLR9, and that the double-stranded CpG-free 72-PD induces IFN-α suggest that the induction of IFN-α from the double-stranded B72-PD is mediated by a cytosolic DNA receptor. This suggests that IFN-α is induced also when a complex of the double-stranded CpG ODN of phosphodiester such as the double-stranded B72-PD is incorporated into the cells having no TLR9.

Example 8

Figure 11:
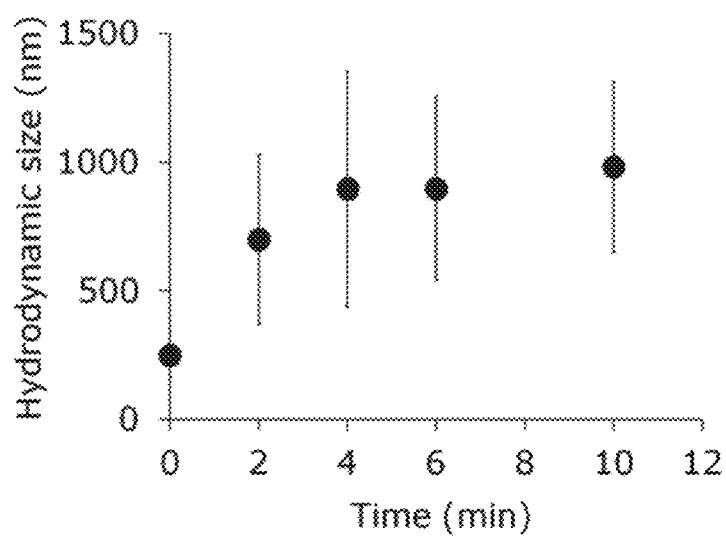
FIG. 11 is a graph showing the size change of Lipofectamine 2000 with time. Lipofectamine 2000 formed conglomerates with the lapse of time.
Figure 12:
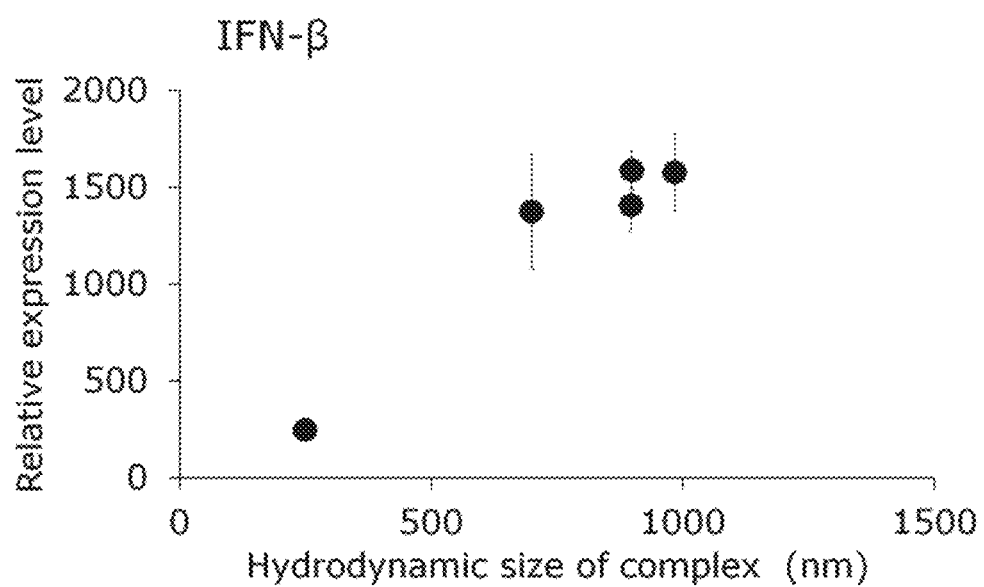
FIG. 12 is a graph showing the relationship between the size of the complex of ds B72-PD with Lipofectamine 2000, and the amount of induced IFN-β. When the complex size was 700 nm or more, high IFN-β inducing potency was exhibited in the stimulation of mouse macrophage-like cells.

Lipofectamine 2000 was dispersed in OptiMEM (Thermo Fisher Scientific Ltd.) at a concentration of 50 µg/ml, and the size was measured by a dynamic light-scattering photometer; as shown in FIG. 11, the size increased with the lapse of time. In the next place, complexes of Lipofectamine 2000 of various sizes after the lapse of different times and ds B72-PD (double strand of SEQ ID NO. 3) were prepared by the method described in Example 1. The size of the complexes thus formed was stable, and was almost the same with that of the original Lipofectamine 2000. These complexes having different sizes were used to stimulate the RAW264.7 cells in the same manner as in Example 1. FIG. 12 shows the relationship between the size of the complex added to the RAW264.7 cells and the amount of induced IFN-β 6 hours after the addition of the complex. The complex of Lipofectamine 2000 and the double-stranded B72-PD showed high IFN-β inducing potency at 700 nm or more.

Example 9

Figure 13:
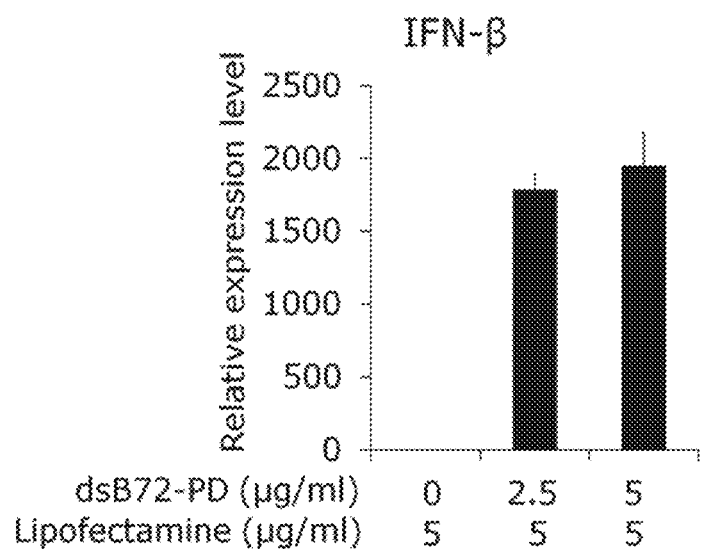
FIG. 13 is a graph showing the influence of the bonding amount of ds B72-PD to Lipofectamine 2000 on the induction of IFN-β. When the concentration of Lipofectamine 2000 in the culture solution was 5 μg/mL, high IFN-β inducing potency was exhibited in the stimulation of mouse macrophage-like cells as long as the bonding amount of ds B72-PD was at least 0.5 or more with reference to the weight of Lipofectamine 2000.

The B72-PD of SEQ ID NO. 3 in Table 2 and a single-stranded ODN that completely complements with the B72-PD were used to prepare a double-stranded ds B72-PD in the same manner as in Example 1. The ds B72-PD and Lipofectamine 2000 were mixed at a weight ratio of 1:2 and 1:1, and complexes having sizes of 737±213 nm and 692±129 nm were obtained. The RAW264.7 cells, which were seeded at a cell density of $3.4\times10^5$ cells/ml and cultured for 16 hours, were stimulated with these complexes for 6 hours at the Lipofectamine 2000 concentration of 5 µg/ml, and the amount of induced IFN-β is shown in FIG. 13. The amounts of the IFN-β induced by these complexes were similar. This result indicates that, when the concentration of Lipofectamine 2000 is 5 µg/ml, the bonding amount of the ds B72-PD in the culture solution should be 0.5 or more with reference to the weight of Lipofectamine 2000.

Example 10

Figure 14:
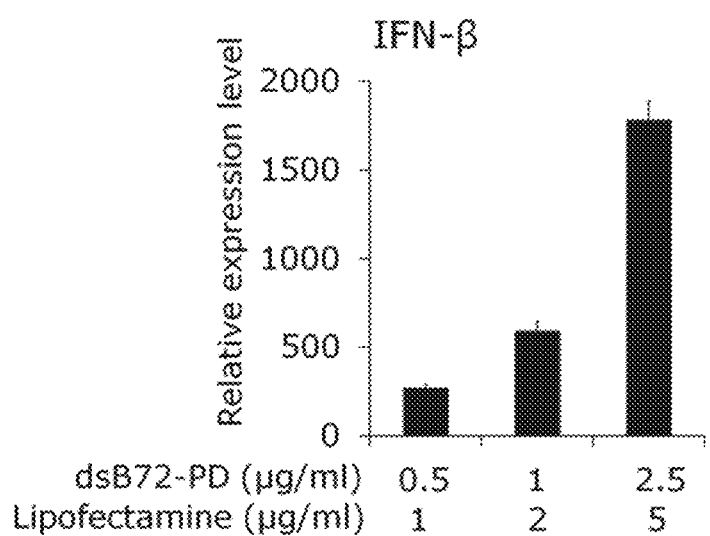
FIG. 14 is a graph showing the influence of the addition concentration of the complex of ds B72-PD with Lipofectamine 2000 on IFN-β. The amount of the IFN-β induced from the mouse macrophage-like cells was dependent on the addition amount of the complex of ds B72-PD with Lipofectamine 2000.

The B72-PD of SEQ ID NO. 3 in Table 2 and a single-stranded CpG ODN that completely complements with the B72-PD were used to prepare a double-stranded ds B72-PD in the same manner as in Example 1. The ds B72-PD and Lipofectamine 2000 were mixed at a weight ratio of 1:2 to form a complex. The size of the complex was 737±213 nm. The complex was added to the RAW264.7 cells, which were seeded at a cell density of $3.4 \times 10^5$ cells/ml and cultured for 16 hours, at the Lipofectamine 2000 concentration of 1, 2, and 5 µg/ml, and the amount of induced IFN-β after 6 hours was measured. As shown in FIG. 14, the higher the addition amount of the complex, the higher the amount of the induction of IFN-β.

Example 11

The phosphodiester-derived single-stranded CpG ODNs having a length of 72 bases shown in Table 5, and single-stranded ODNs having the sequence complementary to the above base sequences were synthesized, and double-stranded CpG ODNs were prepared by the method described in Example 1. The CpG ODNs of SEQ ID Nos. 18 to 22 shown in Table 5 have the partially modified base sequence of B72-PD of SEQ ID NO. 3 in Table 2, and the modified base is indicated by a double underline. The B72M1-PD of SEQ ID NO. 18 in Table 5 is different from the B72-PD of SEQ ID NO. 3 in Table 2 in five base sequences. The B72M2-PD of SEQ ID NO. 19 in Table 5 is different from the B72-PD of SEQ ID NO. 3 in Table 2 in seven base sequences. The B72M3-PD and B72M4-PD of SEQ ID Nos. 20 and 21 in Table 5 are different from the B72-PD of SEQ ID NO. 3 in Table 2 in 12 base sequences. The B72M5-PD of SEQ ID NO. 22 in Table 5 is different from the B72-PD of SEQ ID NO. 3 in Table 2 in 14 base sequences.

TABLE 5

SEQ ID NO. 18
B72M1-PD (single-stranded CpG ODN of 72 bases in
length wherein all nucleotides are phospho-
diester.) Different from B72-PD of SEQ ID NO. 3
at the bases indicated with double underlines.)
5'-TCGTCGTTTTGTCGTTTTGTCGTTTCGTCGTTTTGTCGTTTTGTCGT
TTCGTCGTTTTGTCGTTCTGTTCAC-3'

SEQ ID NO. 19
B72M2-PD (single-stranded CpG ODN of 72 bases in
length wherein all nucleotides are phosphodiester.
Different from B72-PD of SEQ ID NO. 3 at the bases
indicated with double underlines.)
5'-TCGTCGTTTTGTCGTTTTGTCGTTTCGTCGTTTTGTCGTTTTGTCGT
TTCGTCGTTTTGTCGTTCTCGTCAC-3'

SEQ ID NO. 20
B72M3-PD (single-stranded CpG ODN of 72 bases in
length wherein all nucleotides are phosphodiester.
Different from B72-PD of SEQ ID NO. 3 at the bases
indicated with double underlines.)
5'-TCGTCGTTTTGTCGTTTTGTCGTTTCGTCGTTCTCGTCACTTGTCGT
TTCGTCGTTTTGTCGTTCTGTTCAC-3'

SEQ ID NO. 21
B72M4-PD (single-stranded CpG ODN of 72 bases in
length wherein all nucleotides are phosphodiester.
Different from B72-PD of SEQ ID NO. 3 at the bases
indicated with double underlines.)
5'-TCGTCGTTTTGTCGTTTTGTCGTTTCGTCGTTTCTGTTCACTGTCGT
TTCGTCGTTTTGTCGTTCTCGTCAC-3'

TABLE 5-continued

SEQ ID NO. 22
B72M5-PD (single-stranded CpG ODN of 72 bases in
length wherein all nucleotides are phosphodiester.
Different from B72-PD of SEQ ID NO. 3 at the bases
indicated with double underlines.)
5'-TCGTCGTTTTGTCGTTTTGTCGTTTCGTCGTTTCTCGTCACTGTCGT
TTCGTCGTTTTGTCGTTCTCGTCAC-3'

Figure 15:
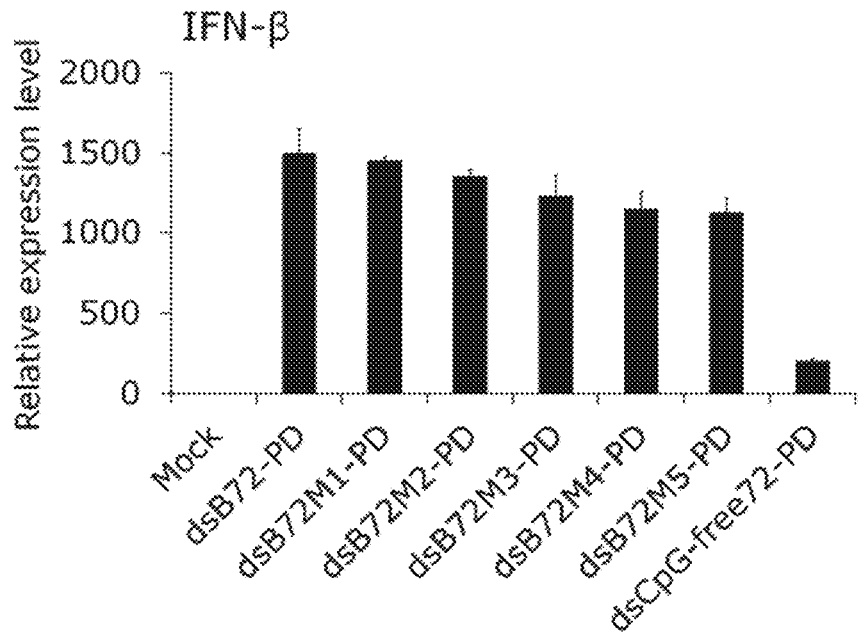
FIG. 15 is a graph showing the induction of IFN-β from the mouse macrophage-like cells by the complexes of the double-stranded CpG ODNs, which were prepared by partially modifying the sequence of ds B72-PD, with Lipofectamine 2000. All the complexes of the double-stranded CpG ODNs (ds B72M1-PD, ds B72M2-PD, ds B72M3-PD, ds B72M4-PD, and ds B72M5-PD) exhibited as high IFN-β inducing potency as the ds B72-PD complex.

The preparation of the complexes of these double-stranded CpG ODNs and Lipofectamine 2000, and stimulation of the RAW264.7 cells by these complexes were carried out by the method described in Example 1. The results are shown in FIG. 15. All of the complexes of the double-stranded CpG ODNs with Lipofectamine 2000 shown in Table 5 showed as high IFN-β inducing potency as the complex of ds B72-PD with Lipofectamine. In addition, these double-stranded CpG ODN complexes showed markedly higher amounts of induced IFN-β than the double-stranded CpG-free 72-PD complex containing no CpG, which indicates that the induction of IFN-β is mostly dependent on TLR9.

Figure 16:
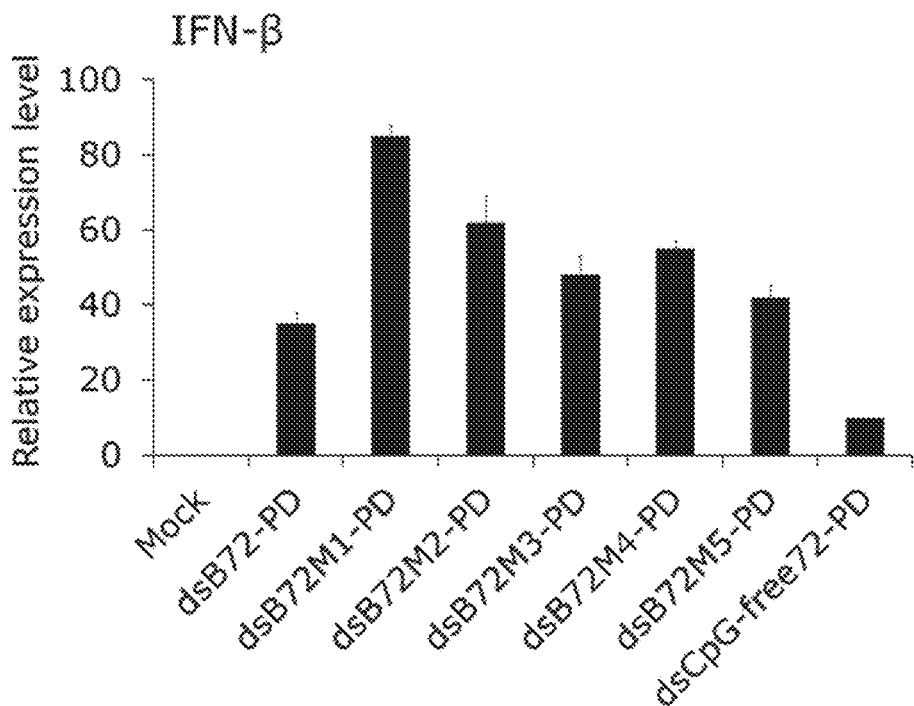
FIG. 16 is a graph showing the induction of IFN-β from the mouse macrophage-like cells by the complexes of the double-stranded CpG ODNs, which were prepared by partially modifying the sequence of ds B72-PD, with DOTAP. All the complexes of the double-stranded CpG ODNs (ds B72M1-PD, ds B72M2-PD, ds B72M3-PD, ds B72M4-PD, and ds B72M5-PD) exhibited higher IFN-β inducing potency than the ds B72-PD complex.

In the next place, the complexes of these double-stranded CpG ODNs with DOTAP were prepared by the method described in Example 5, and the RAW264.7 cells were stimulated by these complexes. The results are shown in FIG. 16. All the complexes of the double-stranded CpG ODNs with DOTAP shown in Table 5 showed IFN-β inducing potency equal to or higher than that of the complex of ds B72-PD with DOTAP.

Example 12

The phosphodiester-derived single-stranded CpG ODNs having a length of 48 bases shown in Table 6, and single-stranded ODNs having the sequence complementary to the above base sequences were synthesized, and double-stranded CpG ODNs were prepared by the method described in Example 1. The CpG ODNs of SEQ ID Nos. 23 to 27 shown in Table 6 have the partially modified base sequence of B48-PD of SEQ ID NO. 2 in Table 2, and the modified base is indicated by a double underline. The B48M1-PD of SEQ ID NO. 23 in Table 6 is different from the B48-PD of SEQ ID NO. 2 in Table 2 in five base sequences. The B48M2-PD of SEQ ID NO. 24 in Table 6 is different from the B48-PD of SEQ ID NO. 2 in Table 2 in seven base sequences. The B48M3-PD and B48M4-PD of SEQ ID Nos. 25 and 26 in Table 6 are different from the B48-PD of SEQ ID NO. 2 in Table 2 in 12 base sequences. The B48M5-PD of SEQ ID NO. 27 in Table 6 is different from the B48-PD of SEQ ID NO. 2 in Table 2 in 14 base sequences. The CpG48-PD of SEQ ID NO. 28 in Table 6 contains 10 CpGs, and the sequences of the two bases before and after the CpG are different from the B48-PD of SEQ ID NO. 2 in Table 2 and SEQ ID Nos. 23 to 27 in Table 6.

TABLE 6

SEQ ID NO. 23
B48M1-PD (single-stranded CpG ODN of 48 bases in
length wherein all nucleotides are phosphodiester.
Different from B48-PD of SEQ ID NO. 2 at the bases
indicated with double underlines.)
5'-TCGTCGTTTTGTCGTTTTGTCGTTTCGTCGTTTTGTCGTTCTGTTCA
C-3'

TABLE 6-continued

SEQ ID NO. 24
B48M2-PD (single-stranded CpG ODN of 48 bases in
length wherein all nucleotides are phosphodiester.
Different from B48-PD of SEQ ID NO. 2 at the bases
indicated with double underlines.)
5'-TCGTCGTTTTGTCGTTTTGTCGTTTCGTCGTTTTGTCGTT<u>CT</u><u>CGTCA</u>
<u>C</u>-3'

SEQ ID NO. 25
B48M3-PD (single-stranded CpG ODN of 48 bases in
length wherein all nucleotides are phosphodiester.
Different from B48-PD of SEQ ID NO. 2 at the bases
indicated with double underlines.)
5'-TCGTCGTT<u>CT</u><u>CGTCAC</u>TTGTCGTTTCGTCGTTTTGTCGTT<u>CT</u>GTT<u>TCA</u>
<u>C</u>-3'

SEQ ID NO. 26
B48M4-PD (single-stranded CpG ODN of 48 bases in
length wherein all nucleotides are phosphodiester.
Different from B48-PD of SEQ ID NO. 2 at the bases
indicated with double underlines.)
5'-TCGTCGTTT<u>CT</u>GTT<u>CAC</u>TGTCGTTTCGTCGTTTTGTCGTT<u>CT</u><u>CGTCA</u>
<u>C</u>-3'

SEQ ID NO. 27
B48M5-PD (single-stranded CpG ODN of 48 bases in
length wherein all nucleotides are phosphodiester.
Different from B48-PD of SEQ ID NO. 2 at the bases
indicated with double underlines.)
5'-TCGTCGTTT<u>CT</u><u>CGTCAC</u>TGTCGTTTCGTCGTTTTGTCGTT<u>CT</u><u>CGTCA</u>
<u>C</u>-3'

SEQ ID NO. 28
CpG48-PD (single-stranded CpG ODN of 48 bases in
length wherein all nucleotides are phosphodiester.
Contains 10 CpGs.)
5'-TCAACGTCTACGAGACGACGTACGTTCGAACGTCCACGTATCGTACG
T-3'

Figure 17:
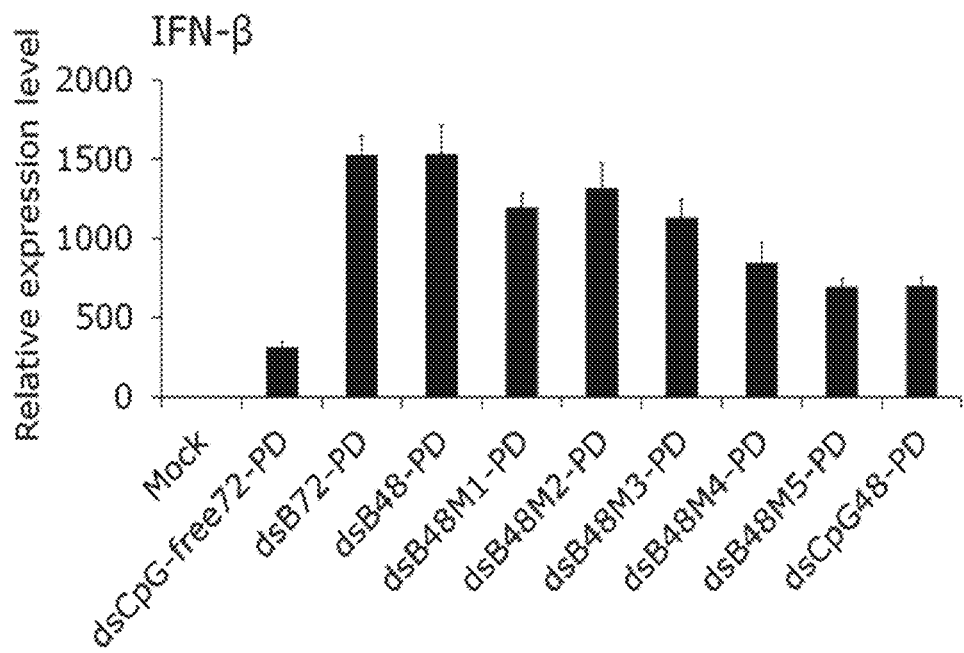
FIG. 17 is a graph showing the induction of IFN-β from the mouse macrophage-like cells by the complexes of the double-stranded CpG ODNs, which were prepared by partially modifying the sequence of ds B48-PD, with Lipofectamine 2000. All the complexes of the double-stranded CpG ODNs (ds 48M1-PD, dsB48M2-PD, ds B48M3-PD, ds B48M4-PD, ds B48M5-PD, and ds CpG48-PD) exhibited the induction of IFN-β mediated by TLR9.

[01.29] The preparation of the complexes of these double-stranded CpG ODNs with Lipofectamine 2000, and irritation of the RAW264.7 cells by these complexes were carried out by the method described in Example 1. The results are shown in FIG. 17. The ds B48M1-PD, ds 48M2-PD, and ds B48M3-PD induced lower amounts of IFN-β than the ds B48-PD, but still showed high level of IFN-β inducing potency. In addition, the ds B48M4-PD, ds B48M5-PD, and ds CpG48-PD showed further lower IFN-β inducing potency, but the potency was higher than ds CpG-free 72-PD, which indicate that the induction of the IFN-β by them is mediated by TLR9.

Example 13

Using the B72-PD of SEQ ID NO. 3 shown in Table 2 and a single-stranded ODN which is completely complementary to the B72-PD, a double-stranded ds B72-PD was prepared by the method described in Example 1. This ds B72-PD and Lipofectamine 2000 were mixed at a weight ratio of 1:1, thus forming a complex. This complex solution was concentrated ten times using Amicon Ultra 0.5 mL Centrifugal Filter (Merck Millipore, Darmstadt, Germany), thus preparing a complex solution containing 50 µg of ds B72-PD in 100 µl. More specifically, 100 µl of the concentrated solution contains a complex of 50 µg of ds B72-PD electrostatically bonded to 50 µg of Lipofectamine 2000. 100 µl of the complex solution containing 50 µg of ds B72-PD, and 100 µl of a solution containing 200 µg of model antigen ovalbumin (OVA) were mixed, and administered to six 6-week age mice (C57BL/6J) in the subcutaneous tissue of back. The ds B72-PD complex and OVA prepared in the same manner as above were administered again to the subcutaneous tissue of back after 7 days. The blood collection was carried out 7 days after the second administration, more specifically, 14 days after the first administration from the caudal vena cava under enflurane inhalation anesthesia. A portion of the collected blood was subjected to EDTA treatment, and the remainder was centrifuged, and then serum was collected from it. The EDTA-treated blood was subjected to hemolysis and fixation treatment, followed by reaction with the PE-Cy5 hamster anti-mouse CD3 antibody, FITC-rat anti-mouse CD8 antibody, and H2-Kb SIINFEKL Class I iTAg™ MHC tetramer, and then the proportion of the OVA-specific CD8-positive T cells was studied by FACS. The OVA-specific IgG1, OVA-specific IgG2a, and OVA-specific IgE contained in the serum were quantitated by ELISA. The proportion of the OVA-specific CD8-positive T cells, and the production amounts of the OVA-specific IgG1, OVA-specific IgG2a, and OVA-specific IgE were compared between the six mice to which 100 µl of a solution containing 200 µg of OVA was administered to subcutaneous tissue of back, twice every 7 days, and the six mice to which nothing was administered.

Figure 18:
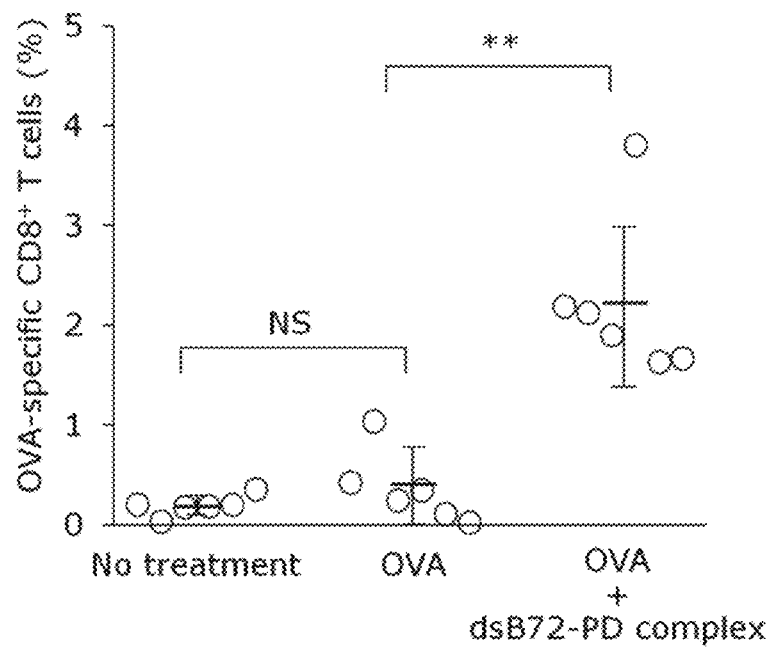
FIG. 18 is a graph showing the induction effect on the OVA-specific CD8-positive T cells by the complex of ds B72-PD with Lipofectamine 2000. The average proportion of the OVA-specific CD8-positive T cells in the CD8-positive T cells in the blood of six mice was significantly higher in the group to which the ds B72-PD complex was administered together with OVA. , $p<0.05$; NS, not significant

FIG. 18 shows the proportion of the OVA-specific CD8-positive T cells. The proportion of the OVA-specific CD8-positive T cells to the CD8-positive T cells in the blood was significantly higher in the mouse group to which the ds B72-PD complex and OVA were administered, than the mouse group to which the OVA was administered alone, indicating the induction effect of the ds B72-PD complex on the antigen-specific CD8-positive T cells. On the other hand, significant increase of the proportion of the OVA-specific CD8-positive T cells was not observed in the mice to which the OVA was administered alone, indicating that the induction of the antigen specific CD8-positive T cells is difficult by the administration of the antigen alone.

Figure 19:
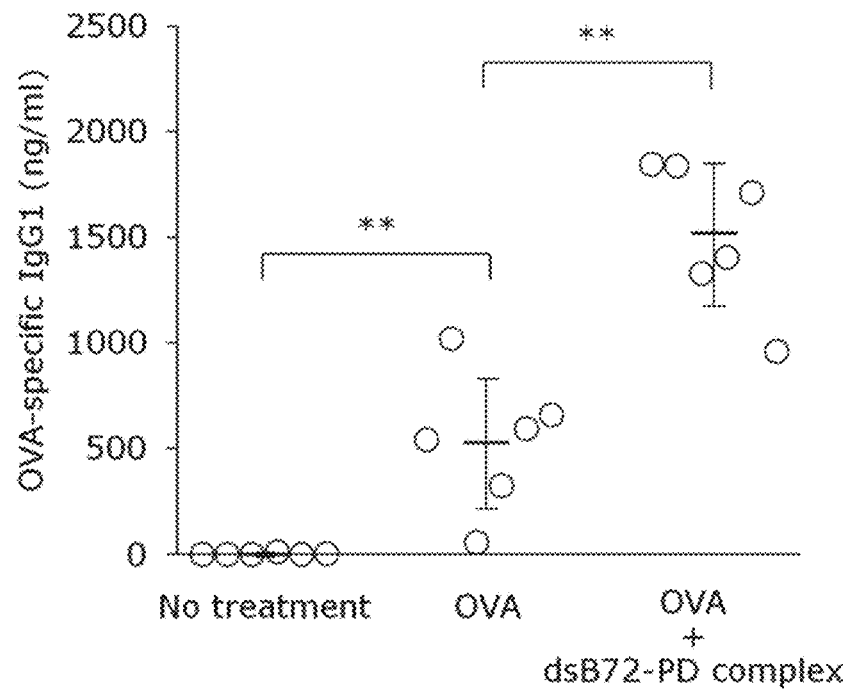
FIG. 19 is a graph showing the production effect on the OVA-specific IgG1 antibody by the complex of ds B72-PD with Lipofectamine 2000. The average amount of the OVA-specific IgG1 antibody in the serum of six mice was significantly higher in the group to which the ds B72-PD complex was administered together with OVA, in comparison with the administration of OVA alone. , $p<0.05$

FIG. 19 shows the amount of production of the OVA-specific IgG1 antibody in the serum. The amount of production of the OVA-specific IgG1 antibody significantly increased also in the mouse group to which the OVA was administered alone. The production of the OVA-specific IgG1 antibody was significantly higher in the mouse group to which the ds B72-PD complex and OVA were administered, than the mouse group to which the OVA was administered alone.

Figure 20:
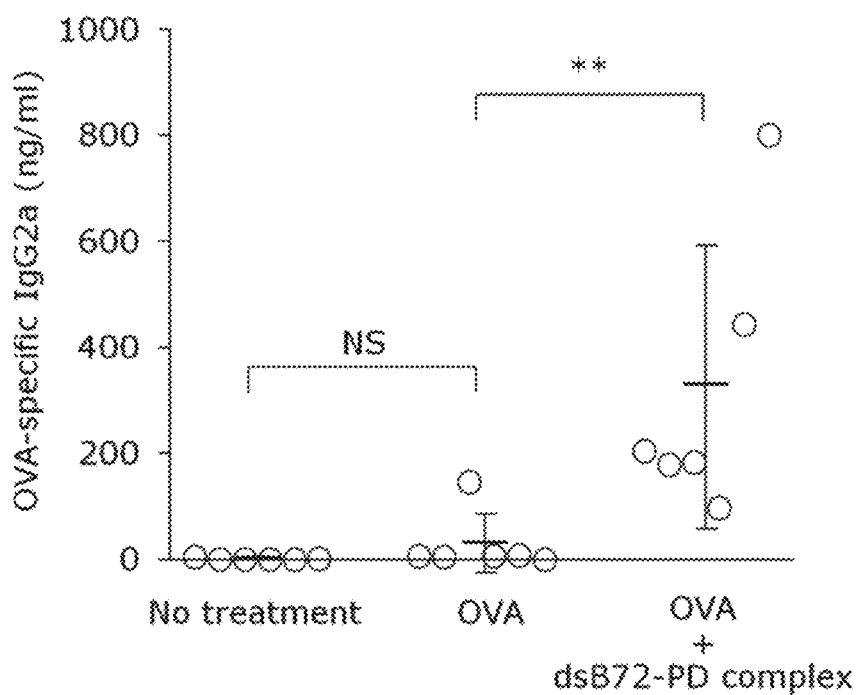
FIG. 20 is a graph showing the production effect on the OVA-specific IgG2a antibody by the complex of ds B72-PD with Lipofectamine 2000. The average amount of the OVA-specific IgG2a antibody in the serum of six mice was significantly higher in the group to which the ds B72-PD complex was administered together with OVA, in comparison with the administration of OVA alone. , $p<0.05$; NS, not significant

FIG. 20 shows the amount of production of the OVA-specific IgG2a antibody in the serum. The production of the OVA-specific IgG2a antibody was significantly higher in the mouse group to which the ds B72-PD complex and OVA were administered, than the mouse group to which the OVA was administered alone. On the other hand, significant increase of the OVA-specific IgG2a was not found in the mouse group to which the OVA was administered alone, which indicates that the induction of the OVA-specific IgG2a is difficult by the administration of the antigen alone.

Figure 21:
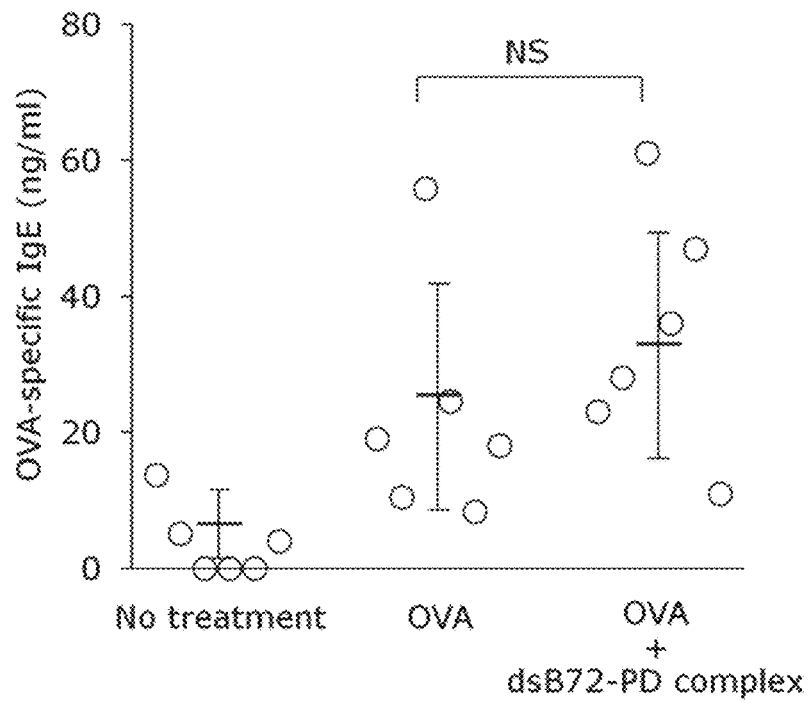
FIG. 21 is a graph showing the production effect on the OVA-specific IgE antibody by the complex of ds B72-PD with Lipofectamine 2000. The average amount of the OVA-specific IgE antibody in the serum of six mice was higher in the group to which the ds B72-PD complex was administered together with OVA, but the increase was not significant. NS, not significant

FIG. 21 shows the production amount of the OVA-specific IgE antibody in the serum. In the mouse group to which the ds B72-PD complex and OVA were administered, the average of the production amount of the OVA-specific IgE antibody increased in comparison with the mouse group to which the OVA was administered alone, but no significant increase was observed.

IgG is involved in delayed immune reaction, and IgE is involved in fast-acting immune reaction. Accordingly, the ds B72-PD complex enhances antigenicity when it is administered together with an antigen, and the combination with a vaccine antigen allows enhancement of its effect. On the other hand, it will not influence fast-acting immune reaction (for example, anaphylaxis), high level of safety is suggested.

In the human peripheral blood mononuclear cells, the major cell species expressing CD80 are likely B cells, monocytes, and dendritic cells, so that the proportions of the CD80-positive cells in the CD20-positive cells (mainly B cells), CD14-positive cells (mainly monocytes), and CD303-positive cells (mainly dendritic cells) were studied. The results are shown in Table 7. The proportion of the CD80-positive cells in the CD20-positive cells was highest for the ds B72-PD complex, which suggests that the ds B72-PD complex activated the B cells, but there was no large increase of the proportion of the CD80-positive cells in the ds CpG-free 72-PD complex in comparison with the untreated one. The proportion of the CD80-positive cells in the CD14-positive cells was highest for the A2216 complex, and a large increase of the CD80-positive cells was observed also in the ds B72-PD complex. Furthermore, for the proportion of the CD80-positive cells in the CD303-positive cells, high CD80 inducing potency was found in all the complexes, and the ds B72-PD complex showed the highest inducing potency.

TABLE 7

Proportion of CD80-positive cells in CD20-positive cells, CD14/positive cells, and CD303-positive cells

|  | Untreated | DOTAP | dsCpG-free72-PD/DOTAP | dsB72-PD/DOTAP | A2216/DOTAP | B24-PT/DOTAP |
|---|---|---|---|---|---|---|
| $CD20^+$ $CD80^+$ (%) | 16.7 ± 1.26 | 14.7 ± 1.13 | 18.6 ± 0.76 | 23.1 ± 0.52 | 21.6 ± 0.85 | 21.7 ± 0.59 |
| $CD14^+$ $CD80^+$ (%) | 27.7 ± 3.40 | 24.3 ± 3.08 | 47.4 ± 3.61 | 57.1 ± 2.90 | 68.1 ± 0.14 | 48.7 ± 1.20 |
| $CD303^+$ $CD80^+$ (%) | 46.6 ± 3.06 | 40.6 ± 5.56 | 73.4 ± 3.04 | 77.3 ± 0.88 | 73.6 ± 1.46 | 73.8 ± 1.08 |

Example 14

Human peripheral blood mononuclear cells (Cellular Technology Limited., OH, USA) were seeded on a 96-well flat-bottom plate at a density of $1\times10^6$ cells/well, and the ds B72-PD, ds CpG-free 72-PD, and ODN2216 (A2216 in Figure.), and B24-PT bonded to DOTAP by electrostatic interaction were added at a concentration of 5 μg/ml (DOTAP concentration was 30 μg/ml). These cells were culture on a medium prepared by mixing RPMI1640 with 10% (v/v) FBS, 10 mM HEPES, and 2 mM L-glutamine. The cells were collected after 6 hours, allowed to react with PerCP/Cy5.5 anti-human CD303 (BDCA-2), FITC anti-human CD14, Alexa Fluor 700 anti-human CD20, and PE anti-human CD80 at room temperature for 15 minutes, washed with PBS, and then the proportion of the CD80-positive cells expressing CD80 as a co-stimulating factor was analyzed by a cell analyzer (SP6800, SONY).

Figure 22:
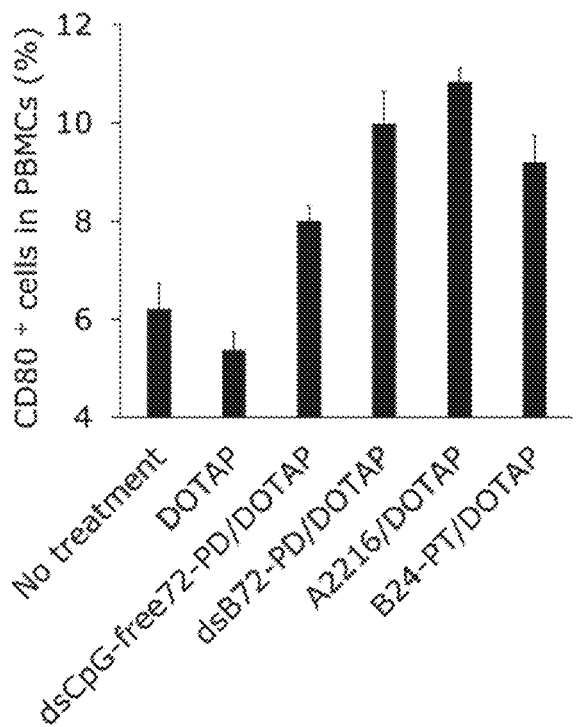
FIG. 22 is a graph showing the proportion of the CD80-positive cells in the human peripheral blood mononuclear cells. CD80 is one of the co-stimulating factors necessary for antigen presentation. The CD80 inducing potency in the ds B72-PD complex was higher than that in the ds CpG-free 72-PD complex, and the inducing potency was equivalent to that of the complex of ODN2216 (A2216 in FIG. 22**), which is CpG-A.

FIG. 22 shows the proportion of the CD80-positive cells in human peripheral blood mononuclear cells. All the DOTAP complexes increased the proportion of the CD80-positive cells in comparison with the untreated one. The proportion of the CD80-positive cells for the ds B72-PD complex was on the same level with that for the complex of A2216, which is a CpG-A, with DOTAP. The proportion of the CD80-positive cells for the ds CpG-free 72-PD complex was lower than that for the ds B72-PD complex or the A2216 complex. In addition, the increase of the proportion of the CD80-positive cells was observed also for the B24-PT complex.

The initiation of the immune reaction by the antigen presenting cells requires two kinds of signals. The first signal is an antigen specific signal mediated by the T lymphocyte receptor, and the second signal is a non-antigen specific signal mediated by a co-stimulating molecule. The ds B72-PD complex efficiently induces CD80 which is a co-stimulating molecule, suggesting that the ds B72-PD complex is effective as an antigenic reinforcer (adjuvant).

Example 15

Figure 23:
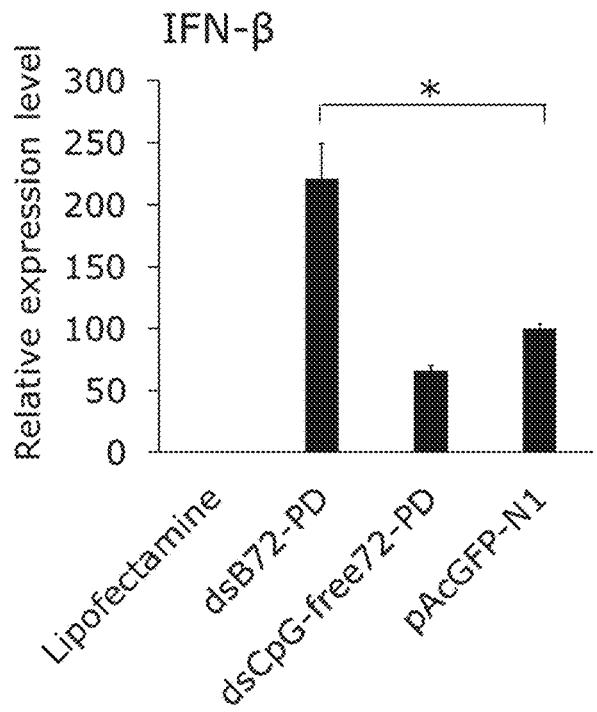
FIG. 23 is a graph showing the comparison of the IFN-β inducing potency from the RAW264.7 cells between the complex of ds B72-PD with Lipofectamine 2000 and the complex of the plasmid vector pAcGFP-N1 with Lipofectamine 2000. The ds B72-PD complex having a linear structure exhibited higher IFN-β inducing potency than the plasmid vector complex having a cyclic structure. *, $p<0.05$
Figure 24:
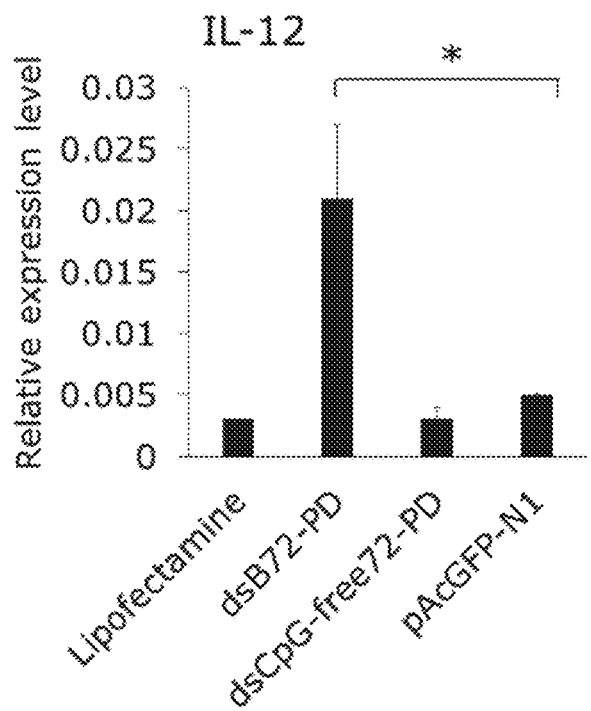
FIG. 24 is a graph showing the comparison of the IL-12 inducing potency from the RAW264.7 cells between the complex of ds B72-PD with Lipofectamine 2000 and the complex of the plasmid vector pAcGFP-N1 with Lipofectamine 2000. The ds B72-PD complex having a linear structure exhibited higher IL-12 inducing potency than the plasmid vector complex having a cyclic structure. *, $p<0.05$

The complexes of Lipofectamine 2000 with ds B72-PD, ds CpG-free 72-PD, and plasmid vector pAcGFP-N1 (TaKaRa Bio, Siga, Japan) were prepared by the method described in Example 1, and the RAW264.7 cells were stimulated by these complexes. FIG. 23 shows the result of the measurement of the amount of induced IFN-β, and FIG. 24 shows the measurement of the amount of induced IL-12 after a lapse of 6 hours. For both of the IFN-β and IL-12, the inducing potency by the ds B72-PD complex was significantly higher than the pAcGFP-N1 complex. The pAcGFP-N1 composed of 4700 base pairs is a phosphodiester double-stranded circular DNA containing CpG, but the linear ds B72-PD complex showed higher IFN-β inducing potency and IL-12 inducing potency than the cyclic double-stranded DNA.

INDUSTRIAL APPLICABILITY

The double-stranded oligonucleotide complex of the present invention has high type-I IFN inducing activity mediated by TLR9, and low inflammatory cytokine inducing activity. The complex involves no risk of side effects by phosphorothioate, is easy to prepare, and thus is useful as, for example, an allergy medicine and a vaccine adjuvant.

[Sequence Listing]

What is claimed is:

1. A linear double-stranded oligonucleotide containing 10 to 100 base pairs, wherein each of the single-stranded oligonucleotides composing said double-stranded oligonucleotide contains 2 to 20 cytosine-guanine sequences (CpG) mediated by phosphodiester, and 90% or more of the bonds between the nucleotides of the single-stranded oligonucleotides are phosphodiester bonds, wherein the single-stranded oligonucleotides do not contain a palindrome sequence.

2. The double-stranded oligonucleotide according to claim 1, wherein all the bonds between the nucleotides of the single-stranded oligonucleotides are phosphodiester bonds.

3. The double-stranded oligonucleotide according to claim 1, wherein the single-stranded oligonucleotide has either of the following base sequence or the sequence wherein one to three bases other than CpG are deleted, substituted, or added:

(SEQ ID NO. 1)
5'-TCGTCGTTTTGTCGTTTTGTCGTT-3'

(SEQ ID NO. 2)
5'-TCGTCGTTTTGTCGTTTTGTCGTTTCGTCGTTTTGTCGTTTTGTCGT
T-3'

(SEQ ID NO. 3)
5'-TCGTCGTTTTGTCGTTTTGTCGTTTCGTCGTTTTGTCGTTTTGTCGT
TTCGTCGTTTTGTCGTTTTGTCGTT-3'

(SEQ ID NO. 4)
5'-ATCGACTCTCGAGCGTTCTC-3'.

4. An immunostimulating oligonucleotide complex comprising a carrier, and the double-stranded oligonucleotide of claim 1 combined with the carrier.

5. The immunostimulating oligonucleotide complex according to claim 4, wherein the carrier is selected from a liposome, a polymer compound, and an inorganic compound.

6. The immunostimulating oligonucleotide complex according to claim 4, wherein the average particle size is 100 nm or more, preferably 250 nm or more, and more preferably 700 nm or more.

7. The immunostimulating oligonucleotide complex according to claim 4, wherein the weight ratio between the double-stranded oligonucleotide and the carrier is from 0.05:1 to 10:1, preferably from 0.1:1 to 10:1, and more preferably from 0.15:1 to 10:1.

8. A vaccine adjuvant comprising the immunostimulating oligonucleotide complex of claim 4.

9. The immunostimulating oligonucleotide complex of claim 4, wherein the complex is for production of a vaccine for prevention of infection of a subject.

10. The immunostimulating oligonucleotide complex of claim 4, wherein the complex is for in the production of a vaccine for treatment or prevention of cancer.

11. The immunostimulating oligonucleotide complex of claim 4, wherein the complex is for treating or preventing cancer.

12. A pharmaceutical composition for treatment or prevention of an allergy, comprising the immunostimulating oligonucleotide complex of claim 4.

13. The pharmaceutical composition according to claim 12, which further comprises an allergen.

14. The immunostimulating oligonucleotide complex of claim 4, wherein the complex is for production of a medicine product for treatment or prevention of an allergy.

15. The immunostimulating oligonucleotide complex of claim 4, wherein the complex is for treatment or prevention of an allergy.

* * * * *